United States Patent
Harris

(10) Patent No.: US 11,242,368 B2
(45) Date of Patent: Feb. 8, 2022

(54) METHODS AND COMPOSITIONS FOR RAPIDLY REPLACING CARDIAC MYOSIN BINDING PROTEIN-C IN SARCOMERES

(71) Applicant: ARIZONA BOARD OF REGENTS ON BEHALF OF THE UNIVERSITY OF ARIZONA, Tucson, AZ (US)

(72) Inventor: Samantha P. Harris, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 2 days.

(21) Appl. No.: 16/579,445

(22) Filed: Sep. 23, 2019

(65) Prior Publication Data

US 2020/0095295 A1 Mar. 26, 2020

Related U.S. Application Data

(60) Provisional application No. 62/734,785, filed on Sep. 21, 2018.

(51) Int. Cl.
*C07K 14/47* (2006.01)
*C12N 15/90* (2006.01)

(52) U.S. Cl.
CPC ............ *C07K 14/47* (2013.01); *C12N 15/907* (2013.01)

(58) Field of Classification Search
None
See application file for complete search history.

(56) References Cited

PUBLICATIONS

Rybakova et al., "Myosin Binding Protein C interaction with Actin", The Journal of Biological Chemistry, vol. 286, No. 3, pp. 2008-2016. (Year: 2011).*

Renz et al., "Determination of AMP-activated protein kinase phosphorylation sites in recombinant protein expressed using the pET28a vector: A cautionary tale", Protein Expression and Purification 66: 181-184. (Year: 2009).*

Kapust and Waugh, "Controlled Intracellular Processing of Fusion Proteins by TEV Protease", Protein Expression and Purification 19:312-218. (Year: 2000).*

Sarikas et al., "Impairment of the ubiquitin-proteasome system by truncated cardiac myosin binding protein C mutants", Cardiovascular Research 66: 33-44. (Year: 2005).*

Previs et al. Molecular Mechanics of Cardiac Myosin-Binding Protein C in Native Thick Filaments. Science vol. 337 Sep. 7, 2012, pp. 1215-1218.

Zakeri et al., PNAS 2012, 109:E690-697.

Reddignton and Howarth, Current Opinion in Chemical Biology 2015, 29:94-99.

* cited by examiner

*Primary Examiner* — Anand U Desai

(74) *Attorney, Agent, or Firm* — Nguyen Tarbet LLC

(57) ABSTRACT

Methods and compositions for rapidly replacing cMyBP-C in sarcomeres featuring the creation of Spy-C mice, which are mice genetically engineered to express cMyBP-C with a protease recognition site and SpyTag peptide introduced into the cMyBP-C gene. In permeabilized myocytes from the Spy-C mice, the cMyBP-C protein can be cleaved at the protease recognition site, and the N-Terminus of cMyBP-C can be removed while the C-terminus remains anchored to the thick filament. A new peptide featuring the SpyCatcher sequence can be covalently bonded to the remaining portion of cMyBP-C, thereby creating a modified cMyBP-C protein. The methods and compositions of the present invention allow for the reconstitution of full-length cMyBP-C at the precise position of native cMyBP-C in the sarcomere and allow for a variety of modifications to be introduced to cMyBP-C in situ.

9 Claims, 2 Drawing Sheets

Figure 1:
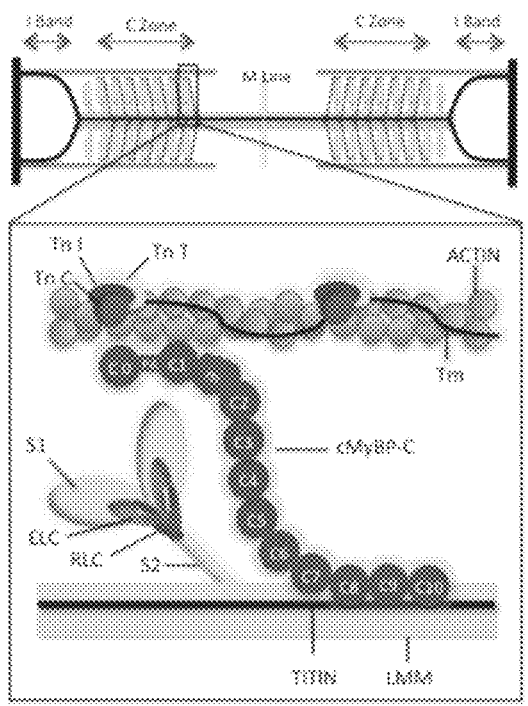

Specification includes a Sequence Listing.

METHODS AND COMPOSITIONS FOR RAPIDLY REPLACING CARDIAC MYOSIN BINDING PROTEIN-C IN SARCOMERES

CROSS-REFERENCES TO RELATED APPLICATIONS

This application is a non-provisional application and claims benefit of U.S. Patent Application No. 62/734,785 filed Sep. 21, 2018, the specification(s) of which is/are incorporated herein in their entirety by reference.

STATEMENT REGARDING FEDERALLY SPONSORED RESEARCH OR DEVELOPMENT

This invention was made with government support under Grant No. R01 HL080367 awarded by NIH. The government has certain rights in the invention.

REFERENCE TO A SEQUENCE LISTING

Applicant asserts that the paper copy of the Sequence Listing is identical to the Sequence Listing in computer readable form found on the accompanying computer file, entitled >>>UNIA_18_20_NP_ST25.txt<<<. The content of the sequence listing is incorporated herein by reference in its entirety.

BACKGROUND OF THE INVENTION

Field of the Invention

The present invention relates to cardiac myosin binding protein-C (cMyBP-C), more particular to methods and compositions for modifying cMyBP-C in sarcomeres, e.g., protein engineering for studying cMyBP-C in sarcomeres.

Background Art

Cardiac myosin binding protein-C (cMyBP-C) is a thick filament-associated protein localized to the C zones of striated muscle sarcomeres. cMyBP-C has a series of 11 folded domains numbered C0-C10, along with a regulatory "M"-domain between C1 and C2. The M-domain contains 3 cardiac-specific phosphorylation sites known to regulate effects of cMyBP-C in response to inotropic agonists, but 14 additional phosphorylation sites have been identified whose function is unknown. The N-terminal domains C0-C2 contribute to the regulatory effects of cMyBP-C on contraction in part by binding to the thin filament in a phosphorylation dependent manner. Domains C8-C10 anchor cMyBP-C to the thick filament.

cMyBP-C is a critical regulator of heart muscle contraction. Mutations in the gene that encodes cMyBP-C, MYPBC3, lead to hypertrophic cardiomyopathy (HCM), a heart muscle disease characterized by an abnormal thickening of the heart muscle.

There are currently no methods to rapidly replace cMyBP-C in sarcomeres, which creates a hurdle to evaluating aspects of cMyBP-C, such as determining the role of phosphorylation sites or the effects of mutations on the function of the protein. Unfortunately, cMyBP-C has an abundance of dynamic interactions that occur with binding partners in the sarcomere, making the study of this protein extremely complex. Also, manipulation of large, thick filaments such as myosin, titin, and cMyBP-C within muscle cells is very difficult.

Others have attempted to manipulate cMyBP-C using AAV methods or adenoviral methods but have achieved limited success. In vitro assays are also limited because they do not preserve the unique localization of cMyBP-C within the sarcomere and often use partial fragments of cMyBP-C (e.g., N-terminal domains only) in excess of the stoichiometry in sarcomeres.

BRIEF SUMMARY OF THE INVENTION

The present invention features methods and compositions for rapidly replacing cMyBP-C in its normal position in sarcomeres. The methods herein feature the use of a single gene-edited mouse model platform (Spy-C mice) that allows for rapid exchange of new combinations of modified or mutant cMyBP-C, such as phosphorylation site mutants, insertions, deletions, fluorescent probes, etc. Briefly, mice are genetically engineered to express cMyBP-C with a protease recognition site and SpyTag peptide introduced into the cMyBP-C gene. (Surprisingly, as discussed below, these mice had overtly normal phenotypes.) The protease recognition site allows the cMyBP-C protein to be cleaved to eliminate the N-Terminus, and the SpyTag peptide allows a different peptide to be attached to the remaining portion of cMyBP-C, thereby creating a modified or recombinant cMyBP-C protein. The methods and compositions of the present invention allow for a variety of modifications to be introduced to cMyBP-C in situ.

The methods and/or compositions of present invention may be used as a research tool, for example to study cMyBP-C (e.g., to study its function, its features, drug interactions, mutations that lead to diseases, etc.), to study diseases such as hypertrophic cardiomyopathy, etc. In certain embodiments the methods and/or compositions of the present invention are used for drug screening assays (e.g., motility assays testing the effects of drugs). The present invention may also be applied to other proteins, such as skeletal muscle MyBP-C isoforms or other sarcomere proteins. There is also the potential to develop cell lines (e.g., stem cells) with a cassette (e.g., TEV/SpyTag cassette) in cMyBP-C or other sarcomere proteins.

Without wishing to limit the present invention to any theory or mechanisms, it is believed that the methods and compositions of the present invention are advantageous because they allow for the rapid introduction of genetic modifications to cMyBP-C in its native position in the sarcomere, allow for the study of cMyBP-C in living cells or animal models, and provide a platform to modify other sarcomeric proteins that cannot be manipulated using traditional methods.

The present invention features methods of producing recombinant cMyBP-C proteins. In certain embodiments, the method comprises introducing a cassette for expressing a first recombinant cMyBP-C into a genome of a host (e.g., mouse, etc.), wherein the cassette comprises MYPBC3, nucleotides encoding a protease recognition site (e.g., TEV protease recognition site) positioned between nucleotides encoding C7 domain and C8 domain, and nucleotides encoding SpyTag positioned in between nucleotides encoding C7 domain and C8 domain (the nucleotides encoding the protease recognition site are 5' to the nucleotides encoding SpyTag); isolating myocytes from the host; introducing to the myocytes a protease that cleaves the first cMyBP-C protein at the protease recognition site to remove its N-terminus; and introducing an N-terminus of cMyBP-C comprising a SpyCatcher peptide C-terminal to the N-terminus of cMyBP-C, wherein the SpyCatcher peptide binds to SpyTag on the first recombinant cMyBP-C to produce a second recombinant cMyBP-C protein.

The present invention features methods of producing a recombinant cMyBP-C protein. In some embodiments, the method comprises introducing into a genome of a host a cassette for expressing a first recombinant cMyBP-C, the first recombinant cMyBP-C being a cMyBP-C peptide with an insertion therein, the insertion comprising a protease recognition site (e.g., TEV protease recognition site or other appropriate protease recognition site) adjacent to and 5' to a SpyTag peptide; isolating myocytes from the host; introducing to the myocytes a protease that cleaves the first cMyBP-C protein at the protease recognition site to remove its N-terminus and expose the SpyTag peptide; introducing a recombinant cMyBP-C N-terminus, the recombinant cMyBP-C N-terminus being at least a portion of cMyBP-C with a SpyCatcher peptide at its C-terminus. The SpyCatcher peptide of the cMyBP-C N-terminus binds to the SpyTag peptide of the first recombinant cMyBP-C to produce a second recombinant cMyBP-C protein. In some embodiments, the host is a mouse. The second recombinant cMyBP-C protein has at least one modified amino acid compared to wild type cMyBP-C.

For the embodiments herein, in some embodiments, the insertion is within or between C7 and C8 domains of cMyBP-C. In some embodiments, the insertion is within or between C2 and C3 domains of cMyBP-C. In some embodiments, the insertion is within or between C3 and C4 domains of cMyBP-C. In some embodiments, the insertion is within or between C4 and C5 domains of cMyBP-C. In some embodiments, the insertion is within or between C5 and C6 domains of cMyBP-C. In some embodiments, the insertion is within or between C6 and C7 domains of cMyBP-C. In some embodiments, the insertion is in between residues VQEILQR (SEQ ID NO: 14) in domain C7 and residues PRLQLPRH (SEQ ID NO: 15) of domain C8 of cMyBP-C. In some embodiments, the insertion is within or between C2 and C8 domains of cMyBP-C.

The present invention also features recombinant proteins comprising cMyBP-C with an insertion therein, the insertion comprises at least a SpyTag peptide adjacent to a protease recognition site. In some embodiments, the protease recognition site is a TEV protease recognition site.

The present invention also features motility assay platforms. In certain embodiments, the assay platform comprises a coverslip with a thick filament disposed thereon, wherein the thick filament comprises a recombinant cMyBP-C protein. The recombinant cMyBP-C protein is produced according to the methods of the present invention. As an example, the thick filaments may be adhered to a SigmaCote-treated (SigmaAldrich) glass coverslip. In some embodiments, the recombinant cMycBP-C protein has at least one modified amino acid compared to wild type cMyBP-C.

The present invention also features nucleic acid sequences encoding cMyBP-C proteins, e.g., recombinant cMyBP-C proteins, etc. In certain embodiments, the nucleic acid sequence comprises MYPBC3, nucleotides encoding a protease recognition site (e.g., TEV protease recognition site) positioned between nucleotides encoding C7 domain and C8 domain, and nucleotides encoding SpyTag positioned in between nucleotides encoding C7 domain and C8 domain (the nucleotides encoding the protease recognition site being 5' to the nucleotides encoding SpyTag).

The present invention also features recombinant proteins, e.g., cMyBP-C recombinant proteins. In certain embodiments, the recombinant protein comprises cMyBP-C with a protease recognition site (e.g., TEV protease recognition site) and a SpyTag peptide positioned in between domain C7 and C8. In certain embodiments, the recombinant protein comprises cMyBP-C with a protease recognition site (e.g., TEV protease recognition site) and a SpyTag peptide positioned in an insertion site in the protein. The insertion site is not limited to a site between domain C7 and domain C8.

The present invention also features genetically engineered hosts (e.g., mice) expressing a recombinant cMyBP-C protein. In some embodiments, the host (e.g., mouse) expresses a recombinant cMyBP-C protein comprising cMyBP-C with a protease recognition site (e.g., TEV protease recognition site) and a SpyTag peptide positioned in between domain C7 and C8. In certain embodiments, the genetically engineered mouse expresses a recombinant cMyBP-C protein with a protease recognition site (e.g., TEV protease recognition site) and SpyTag peptide position in an insertion site in the protein. The insertion site is not limited to between domains C7 and C8. In certain embodiments, the protease recognition site is N-terminal to the SpyTag peptide. In certain embodiments, the protease recognition site is positioned directly next to the SpyTag peptide.

The present invention also features methods of evaluating a mutation in cMyBP-C. In certain embodiments, the method comprises producing a thick filament expressing a recombinant cMyBP-C peptide according to the present invention, wherein the recombinant cMyBP-C has at least one modification compared to wild type cMyBP-C; attaching the thick filament to a substrate; introducing fluorescently labeled actin filaments to the thick filament on the substrate; and tracking sliding of the actin filaments along the thick filaments. In certain embodiments, if the sliding of the actin filaments is different than that observed using thick filaments with wild type cMyBP-C, then at least one modification in the recombinant cMyBP-C has an impact on actin filament sliding. In certain embodiments, the thick filament is obtained from a host (e.g., mouse) in which the recombinant cMyBP-C is expressed. In certain embodiments, the thick filament is obtained from permeabilized myocytes derived from the host (e.g., mouse) in which the recombinant cMyBP-C is expressed.

The present invention also features methods of evaluating effects of a drug. In some embodiments, the method comprises producing a thick filament expressing a recombinant cMyBP-C peptide according to the present invention, wherein the recombinant cMyBP-C has at least one modification compared to wild type cMyBP-C; attaching the thick filament to a substrate; introducing fluorescently labeled actin filaments to the thick filament on the substrate; introducing a drug to the thick filament on the substrate; and tracking sliding of the actin filaments along the thick filaments. In certain embodiments, if the sliding of the actin filaments is different than that observed when a control is introduced to the thick filament on the substrate in lieu of the drug, then the drug has an impact on actin filament sliding. In some embodiments, the thick filament is obtained from a host in which the recombinant cMyBP-C is expressed. In some embodiments, the thick filament is obtained from permeabilized myocytes derived from the host in which the recombinant cMyBP-C is expressed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1. Shows a schematic view of the structure of cMyBP-C as a series of 11 folded domains (purple circles) numbered C0-C10 along with the regulatory M-domain between C1 and C2. The M-domain contains 3 cardiac-specific phosphorylation sites known to regulate effects of cMyBP-C in response to inotropic agonists, but 14 additional phosphorylation sites have been identified whose function is unknown. The N'-terminal domains C0-C2 contribute to the regulatory effects of cMyBP-C on contraction in part by binding to the thin filament in a phosphorylation dependent manner. Domains C8-C10 anchor cMyBP-C to the thick filament.

Figure 2:
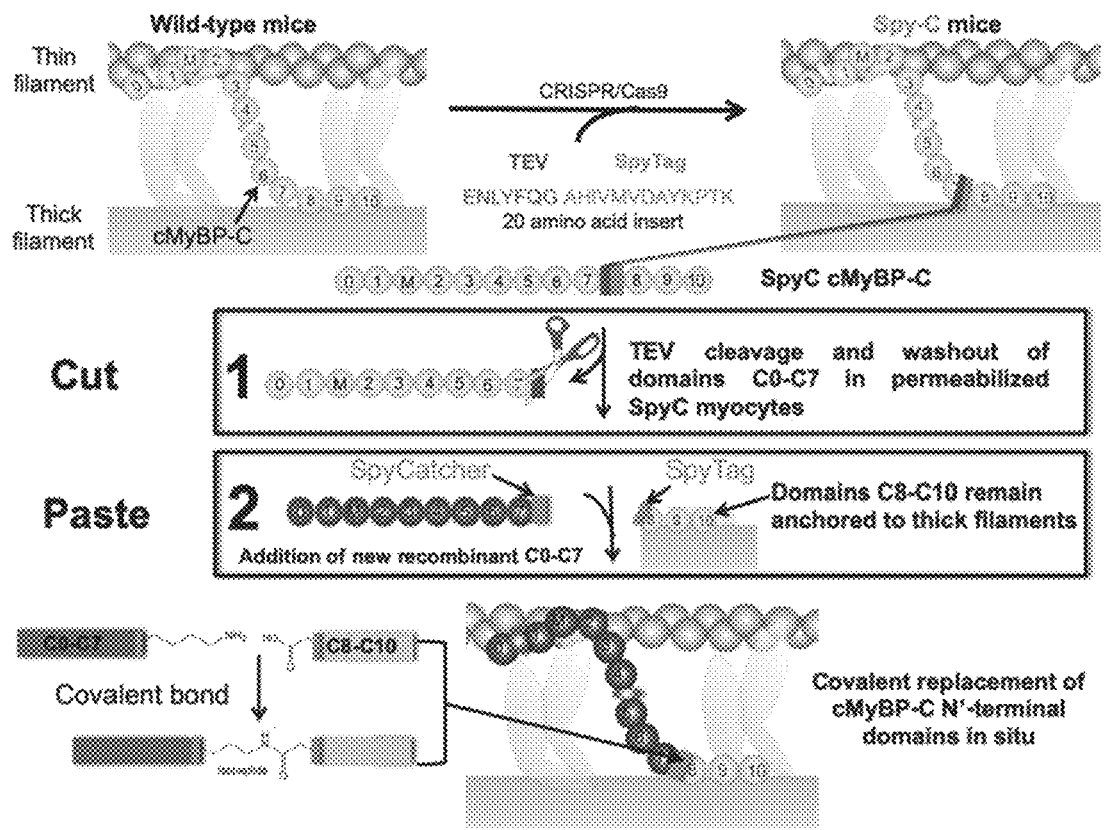

FIG. 2 shows a schematic view of the method of the present invention, e.g., the rapid exchange of cMyBP-C in Spy-C permeabilized myocytes. Spy-C mice express cMyBP-C with a TEV protease recognition site (blue rectangle) and a SpyTag sequence (orange rectangle) inserted between domains C7 and C8. (1) TEV cleavage of Spy-C cMyBP-C in permeabilized myocytes first removes domains C0-C7, which (2) are subsequently replaced by new recombinant C0-C7 domains (purple) containing desired phosphorylation site mutations (example sites in C0, M, and C4 indicated by red asterisks). The new C0-C7 domains covalently attach to C8-C10 via the SpyCatcher and SpyTag bond. Because domains C8-C10 remain anchored to the thick filament after TEV cleavage, the Spy-C method efficiently achieves replacement of cMyBP-C in situ.

Figure 3:
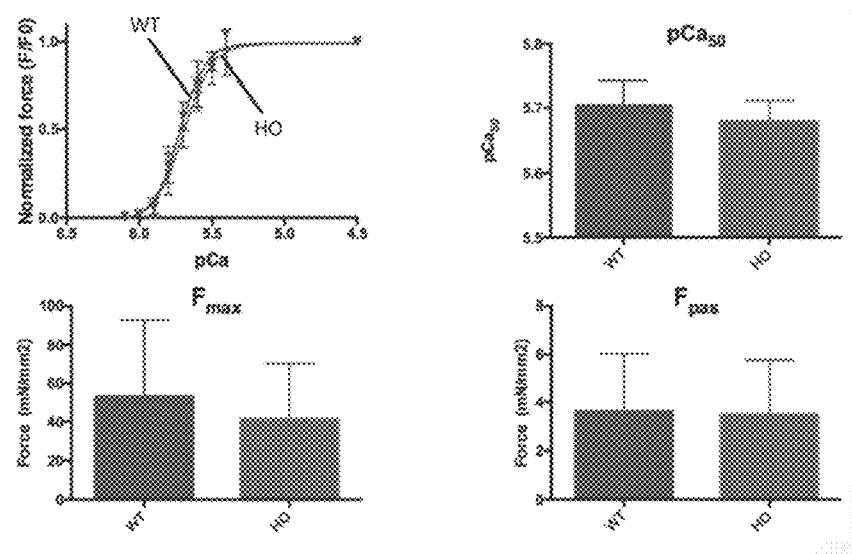

FIG. 3 shows force measurements in cardiomyocytes from wild type (WT) and homozygous (HO) Spy-C mice, demonstrating overtly normal force generation in cardiomyocytes from Spy-C mice. Top left panel shows normal tension-pCa relationships in WT and HO myocytes, while the top right panel shows summary data illustrating that the midpoints of the tension-pCa relationships are not different. Bottom panels show that maximal force ($F_{max}$) and passive tension ($F_{pas}$) also are not different between WT and HO myocytes.

Figure 4:
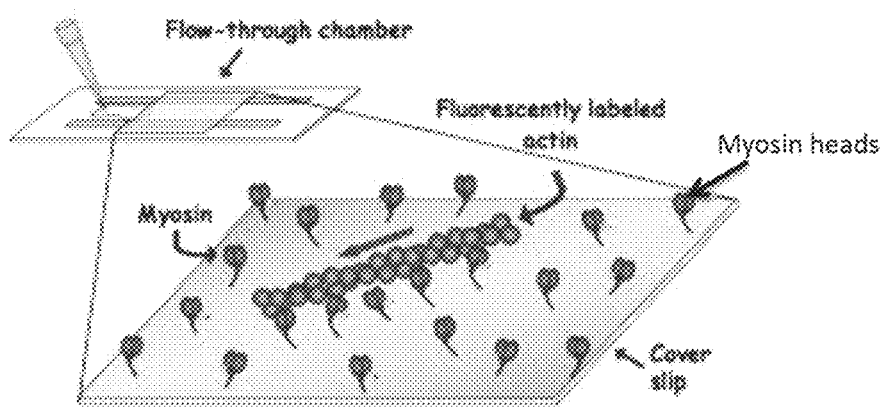

FIG. 4 shows a typical in vitro motility assay (prior art).

Figure 5:
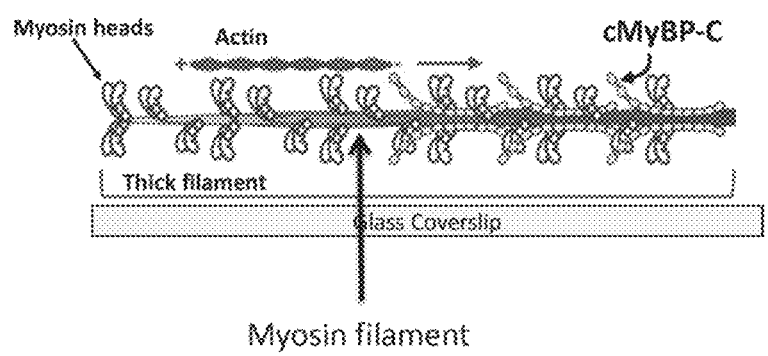

FIG. 5 shows a motility assay using thick filaments, highlighting where cMyBP-C proteins (e.g., recombinant cMyBP-C proteins made using the methods and compositions herein) are located (image source: Previs et al., Science 2012, 337:1215-1218). Myosin molecules are maintained in their native filamentous state (blue). Full-length cMyBP-C (orange) can be retained at its proper locations on thick filaments.

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory. Press, 1999, *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

CRISPR/Cas9: A genome editing tool that enables the editing of parts of the genome by removing, adding, or altering sections of the DNA sequence. Cas9 is an enzyme that acts as a pair of molecular scissors to cut the two stands of DNA at a specific location in the genome so that other DNA can be added or removed. Guide RNA (gRNA) is a small piece of pre-designed RNA located within a longer RNA scaffold. The scaffold part binds to DNA and the pre-designed sequence guides Cas9 to the right part of the genome. The gRNA has a sequence that is complementary to the target DNA sequence. After the DNA is cut, the cell recognizes the DNA damage and tries to repair it. The DNA repair machinery can be used to introduce changes to the gene.

Modification: Changes to a protein sequence, structure, etc., or changes to a nucleic acid sequence, etc. As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

Recombinant nucleic acid: A nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Recombinant protein: For a recombinant nucleic acid, see "Recombinant Nucleic Acid" above. A recombinant protein or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. Recombinant proteins may be made in cells transduced, transfected, or transformed with genetic elements to direct the synthesis of the heterologous protein. They may also be made in cell-free systems.

DETAILED DESCRIPTION OF THE INVENTION

The present invention features methods and compositions for rapidly replacing cMyBP-C in its normal position in sarcomeres. The methods herein feature the use of a gene-edited mouse model platform that allows for rapid exchange of new combinations of modified or mutant cMyBP-C, such as phosphorylation site mutants, insertions, deletions, fluorescent probes, etc.

Split Peptide Pairs

The present invention features the use of a split peptide pair, e.g., a pair of peptides derived from the splitting of a protein into two halves, each with reactive residues. The split peptide pair is engineered to recombine and form covalent bonds (irreversible isopeptide linkages), thereby creating a new fusion protein. A non-limiting example of a split peptide pair includes SpyCatcher/SpyTag. SpyCatcher and SpyTag are well known to one of ordinary skill in the art. SpyTag and SpyCatcher were generating by splitting the CnaB2 domain from the fibronectin-binding protein FbaB from *Streptococcus pyogenes* (Spy). CnaB2 was split into a 13 residue peptide (SpyTag) and the 116 residue complementary domain (SpyCatcher). These two parts spontaneously reconstitute to form an isopeptide bond under a range of temperatures, pH values, buffers, and even with non-ionic detergents. SpyTag and SpyCatcher function well when fused at either the N-terminus or C-terminus (see Zakeri et al., PNAS 2012, 109:E690-697; Reddington and Howarth, Current Opinion in Chemical Biology 2015, 29:94-99. SpyCatcher/SpyTag has been used previously to create genetic fusions including several platform technologies such as synthetic vaccine production and catalytic circulation.

As used in the present invention. The SpyCatcher and SpyTag pair form a spontaneous isopeptide bond between a reactive lysine of SpyCatcher and a reactive aspartate of SpyTag when each half of the pair is expressed as a fusion protein with cMyBP-C. The present invention is not limited to SpyCatcher/SpyTag. Any appropriate split peptide pair that is currently available or that may be developed in the future may be contemplated. For example, in certain embodiments, the split peptide pair is SnoopCatcher/SnoopTag.

Spy-C Method

In the present invention, the SpyCatcher/SpyTag technology was applied to generically engineered mice (see FIG. 2). Spy-C mice were created using CRISPR/Cas9 gene editing to introduce a protease recognition site (e.g., tobacco etch virus (TEV) protease recognition site, blue rectangle in FIG. 2) and a SpyTag sequence (orange rectangle in FIG. 2) in the linker between domains C7 and C8 of cMyBP-C. The protease recognition site allows a portion (e.g., the N-terminus) of cMyBP-C to be cut and removed, and the SpyTag sequence allows another peptide with a SpyCatcher sequence to be attached to the remaining portion of cMyBP-C. Note that TEV is highly specific for a consensus sequence. The sequence is rare in mammalian proteins.

To achieve rapid exchange of cMyBP-C in permeabilized myocytes, Spy-C cMyBP-C was cleaved at the TEV site. Domains C0-C7 of Spy-C cMyBP-C were then readily washed out and replaced with novel recombinant cMyBP-C-SpyCatcher containing desired phosphorylation site mutations by adding proteins directly to the bath surrounding the permeabilized myocytes. Added C0-C7-SpyCatcher (purple rectangle in FIG. 2) formed a permanent covalent bond with SpyTag (orange rectangle in FIG. 2) encoded at the beginning of domains C8-C10. Domains C8-C10 remained anchored to the thick filament because these domains contain the major binding sites for myosin and titin and densities attributable to domains C8-C10 are visible in EM reconstructions of isolated thick filaments. Note that other insertion sites may be possible.

By fusing the SpyCatcher sequence to new recombinant cMyBP-C N-terminal sequences, it is possible to reconstitute full-length cMyBP-C at the precise position of native cMyBP-C in the sarcomere. Thus, the present invention provides methods for efficiently cutting and pasting cMyBP-C in situ to introduce virtually any desired modification (e.g., point mutations, FRET probes, etc.) to study cMyBP-C interactions with its binding partners in sarcomeres or to provide recombinant cMyBP-C peptides for various purposes.

It was surprisingly found that the Spy-C mice generated were phenotypically normal. Given the importance of the cMyBP-C protein, it was expected that disruption of the cMyBP-C protein would have deleterious effects that might preclude the usefulness of the mouse model. However, echocardiography demonstrated the Spy-C mice had no overt cardiac phenotype up to 12 months of age in founders or progeny. Further, cMyBP-C expression was normal and cMyBP-C was properly localized in sarcomeres in Spy-C mice. FIG. 3 shows force measurements in wild type and Spy-C mice, demonstrating overtly normal force generation in cardiomyocytes from Spy-C mice. Inventors were also surprised that the protein was not destabilized by the insertion of the TEV protease site and SpyTag between the C7-C8 regions. There is not much known about the C-terminal end of the cMyBP-C protein, so it was not clear if the insertion would work, or where the insertion should be placed.

Non-limiting examples of sequences encoding modified cMyBP-C proteins are included in Table 1. SEQ ID NO: 1 is a cDNA sequence for wild-type cMyBP-C C0-C7 domains with SpyCatcher followed by a TEV recognition site, His Tag, and Stop codon. SEQ ID NO: 1 is used to make C0-C7-sc replacement domains after TEV cleavage of cMyBP-C in myocytes from Spy-C mice. SEQ: ID NO: 2 is a cDNA sequence for cMyBP-C C0-C7 domains containing the [E330K] mutation with SpyCatcher followed by a TEV recognition site, His Tag, and Stop codon. SEQ: ID NO: 2 is used to make C0-C7-sc replacement proteins with the specified mutation after TEV cleavage of cMyBP-C in myocytes from Spy-C mice. SEQ ID NO: 3 is a cDNA sequence for cMyBP-C C0-C7 domains containing the [L348P] mutation with SpyCatcher followed by a TEV recognition site, His Tag, and Stop codon. SEQ ID NO: 3 is used to make C0-C7-sc replacement proteins with the specified mutation after TEV cleavage of cMyBP-C in myocytes from Spy-C mice.

TABLE 1

| Description | Sequence |
| --- | --- |
| SEQ ID NO: 1 | ATGCCGGAGCCGGGTAAAAAGCCGGTTAGCGCGTTCAACAAAAAACCGCGTAGCGCGGAAG TGACCGCGGGTAGCGCGGCGGTGTTTGAGGCGGAAACCGAGCGTAGCGGCGTTAAAGTGC GTTGGCAACGTGACGGTAGCGATATTACCGCGAACGATAAATACGGTCTGGCGGCGGAAGG CAAGCGTCACACCCTGACCGTTCGTGATGCGAGCCCGGACGATCAGGGTAGCTATGCGGTG ATCGCGGGCAGCAGCAAGGTGAAATTTGACCTGAAAGTTACCGAGCCGGCTCCGCCGGAAA AAGCGGAAAGCGAGGTGGCGCCGGGTGCGCCGAAGGAAGTTCCGGCGCCGGCGACCGAG CTGGAGGAAAGCGTGAGCAGCCCGGAAGGCAGCGTTAGCGTGACCCAGGATGGTAGCGCG GCGGAACATCAAGGTGCGCCGGATGATCCGATCGGTCTGTTCCTGATGCGTCCGCAAGACG GTGAGGTTACCGTGGGTGGCAGCATTGTGTTTAGCGCGCGTGTTGCGGGTGCGAGCCTGCT GAAACCGCCGGTGGTTAAGTGGTTCAAGGGCAAATGGGTGGATCTGAGCAGCAAAGTTGGT CAGCACCTGCAACTGCACGACAGCTACGATCGTGCGAGCAAGGTTTACCTGTTCGAACTGCA CATTACCGATGCGCAGACCACCAGCGCGGGTGGCTACCGTTGCGAGGTTAGCACCAAGGAC AAATTCGATAGCTGCAACTTTAACCTGACCGTGCACGAAGCGATCGGTAGCGGCGACCTGG ATCTGCGTAGCGCGTTTCGTCGTACCAGCCTGCGGGTGCGGGTCGTCGTACCAGCGACAG CCATGAGGATGCGGGCACCCTGGATTTCAGCAGCCTGCTGAAGAAACGTGATAGCTTTCGT CGTGACAGCAAACTGGAAGCGCCGGCGGAGGAAGACGTTTGGGAGATCCTGCGTCAAGCT CCGCCGAGCGAATACGAGCGTATTGCGTTCCAGCACGGTGTGACCGATCTGCGTGGCATGC TGAAGCGTCTGAAGGGTATGAAGCAGGACGAAAAGAAAAGCACCGCGTTTCAGAAGAAACT GGAGCCGGCGTATCAAGTGAACAAAGGCCACAAGATCCGTCTGACCGTGGAACTGGCGGAC CCGGATGCGGAAGTGAAATGGCTGAAGAACGGCCAGGAAATCCAAATGAGCGGTAGCAAAT ACATTTTCGAGAGCGTTGGTGCGAAGCGTACCCTGACCATTAGCCAATGCAGCCTGGCGGA CGATGCGGCGTATCAGTGCGTGGTTGGTGGCGAGAAATGCAGCACCGAACTGTTCGTGAAG GAGCCGCCGGTTCTGATCACCCGTAGCCTGGAAGATCAGCTGGTTATGGTGGGTCAACGTG TGGAATTTGAGTGCGAAGTTAGCGAGGAAGGCGCGCAAGTGAAATGGCTGAAGGACGGTGT TGAGCTGACCCGTGAGGAAACCTTCAAATACCGTTTTAAGAAAGATGGTCGTAAGCACCACC TGATCATTAACGAAGCGACCCTGGAGGATGCGGGTCACTATGCGGTTCGTACCAGCGGTGG CCAGAGCCTGCGGAACTGATCGTGCAAGAAAAGAAACTGGAAGTGTATCAGAGCATTGCG GATCTGGCGGTGGGTGCGAAAGACCAGGCGGTGTTCAAGTGCGAAGTTAGCGATGAGAACG TTCGTGGTGTGTGGCTGAAAAACGGCAAGGAGCTGGTTCCGGACAACCGTATCAAAGTGAG CCACATTGGTCGTGTTCACAAGCTGACCATCGACGATGTTACCCCGGCGGACGAAGCGGAT TATAGCTTCGTGCCGGAGGCTTTGCGTGCAACCTGAGCGCGAAACTGCACTTCATGGAAG TGAAGATCGACTTTGTTCCGCGTCAGGAGCCGCCGAAAATTCATCTGGATTGCCCGGGTAGC ACCCCGGACACCATTGTGGTTGTGGCGGGTAACAAACTGCGTCTGGATGTGCCGATTAGCG GCGACCCGGCGCCGACCGTTGTGTGGCAGAAGACCGTGACCCAAGGTAAGAAAGCGAGCA CCGGTCCGCACCCGGATGCGCCGGAGGATGCGGGTGCGGACGAGGAATGGGTTTTCGATA AGAAACTGCTGTGCGAAACCGAAGGCCGTGTTCGTGTGGAAACCACCAAGGATCGTAGCGT TTTTACCGTGGAGGGCGCGGAGAAAGAAGACGAGGGTGTTTACACCGTTACCGTGAAGAAC CCGGTGGGTGAAGACCAGGTTAACCTGACCGTTAAAGTTATTGATGTTCCGGATGCGCCGG CGGCGCCGAAGATTAGCAACGTGGGTGAAGATAGCTGCACCGTTCAATGGGAGCCGCCGG CGTATGATGGTGGCCAGCCGGTGCTGGGCTATATCCTGGAGCGTAAGAAAAAGAAAAGCTA TCGTTGGATGCGTCTGAACTTCGACCTGCTGCGTGAACTGAGCCACGAGGCGCGTCGTATG ATTGAAGGTGTTGCGTACGAGATGCGTGTTTATGCGGTGAACGCGGTTGGTATGAGCCGTC CGAGCCCGGCGAGCCAGCCGTTTATGCCGATTGGTCCGCCGGGTGAACCGACCCACCTGG CGGTGGAGGACGTTAGCGATACCACCGTGAGCCTGAAATGGCGTCCGCCGGAACGTGTTG GTGCGGGTGGCCTGGATGGCTACAGCGTGGAATATTGCCAAGAGGGCTGCAGCGAATGGA CCCCGGCGCTGCAGGGTCTGACCGAGCGTACCAGCATGCTGGTTAAAGACCTGCCGACCG GTGCGCGTCTGCTGTTCCGTGTGCGTGCGCATAACGTTGCGGGTCCGGGTGGCCCGATCGT GACCAAGGAACCGGTTACCGTGCAGGAGATT[AGCGGTGATAGCGCGACCCACATTAAATTT AGCAAGCGTGACGAGGATGGTAAAGAACTGGCGGGCGCGACCATGGAACTGCGTGACAGC AGCGGCAAGACCATCAGCACCTGGATTAGCGATGGTCAGGTTAAAGACTTCTACCTGTATCC GGGCAAGTACACCTTTGTGGAAACCGCGGCGCCGGATGGTTATGAGGTGGCGACCGCGAT CACCTTCACCGTTAACGAGCAGGGTCAAGTTACCGTGAACGGTAAAGCGACCAAGGGC][GA GAATCTGTATTTCCAGGGT][CATCACCACCACCATCAC]TAA |
| SEQ ID NO: 2 | ATGCCGGAGCCGGGTAAAAAGCCGGTTAGCGCGTTCAACAAAAAACCGCGTAGCGCGGAAG TGACCGCGGGTAGCGCGGCGGTGTTTGAGGCGGAAACCGAGCGTAGCGGCGTTAAAGTGC GTTGGCAACGTGACGGTAGCGATATTACCGCGAACGATAAATACGGTCTGGCGGCGGAAGG CAAGCGTCACACCCTGACCGTTCGTGATGCGAGCCCGGACGATCAGGGTAGCTATGCGGTG ATCGCGGGCAGCAGCAAGGTGAAATTTGACCTGAAAGTTACCGAGCCGGCTCCGCCGGAAA |

TABLE 1-continued

| Description | Sequence |
|---|---|
| | AAGCGGAAAGCGAGGTGGCGCCGGGTGCGCCGAAGGAAGTTCCGGCGCCGGCGACCGAG<br>CTGGAGGAAAGCGTGAGCAGCCCGGAAGGCAGCGTTAGCGTGACCCAGGATGGTAGCGCG<br>GCGGAACATCAAGGTGCGCCGGATGATCCGATCGGTCTGTTCCTGATGCGTCCGCAAGACG<br>GTGAGGTTACCGTGGGTGGCAGCATTGTGTTTAGCGCGCGTGTTGCGGGTGCGAGCCTGCT<br>GAAACCGCCGGTGGTTAAGTGGTTCAAGGGCAAATGGGTGGATCTGAGCAGCAAAGTTGGT<br>CAGCACCTGCAACTGCACGACAGCTACGATCGTGCGAGCAAGGTTTACCTGTTCGAACTGCA<br>CATTACCGATGCGCAGACCACCAGCGCGGGTGGCTACCGTTGCGAGGTTAGCACCAAGGAC<br>AAATTCGATAGCTGCAACTTTAACCTGACCGTGCACGAAGCGATCGGTAGCGGCGACCTGG<br>ATCTGCGTAGCGCGTTTCGTCGTACCAGCCTGGCGGGTGCGGGTCGTCGTACCAGCGACAG<br>CCATGAGGATGCGGGCACCCTGGATTTCAGCAGCCTGCTGAAGAAACGTGATAGCTTTCGT<br>CGTGACAGCAAACTGGAAGCGCCGGCGGAGGAAGACGTTTGGGAGATCCTGCGTCAAGCT<br>CCGCC[AAG]CGAATACGAGCGTATTGCGTTCCAGCACGGTGTGACCGATCTGCGTGGCATG<br>CTGAAGCGTCTGAAGGGTATGAAGCAGGACGAAAAGAAAAGCACCGCGTTTCAGAAGAAAC<br>TGGAGCCGGCGTATCAAGTGAACAAAGGCCACAAGATCCGTCTGACCGTGGAACTGGCGGA<br>CCCGGATGCGGAAGTGAAATGGCTGAAGAACGGCCAGGAAATCCAAATGAGCGGTAGCAAA<br>TACATTTTCGAGAGCGTTGGTGCGAAGCGTACCCTGACCATTAGCCAATGCAGCCTGGCGG<br>ACGATGCGGCGTATCAGTGCGTGGTTGGTGGCGAGAAATGCAGCACCGAACTGTTCGTGAA<br>GGAGCCGCCGGTTCTGATCACCCGTAGCCTGGAAGATCAGCTGGTTATGGTGGGTCAACGT<br>GTGGAATTTGAGTGCGAAGTTAGCGAGGAAGGCGCGCAAGTGAATTGGCTGAAGGACGGTG<br>TTGAGCTGACCCGTGAGGAAACCTTCAAATACCGTTTTAAGAAAGATGGTCGTAAGCACCAC<br>CTGATCATTAACGAAGCGACCCTGGAGGATGCGGGTCACTATGCGGTTCGTACCAGCGGTG<br>GCCAGAGCCTGCGGAACTGATCGTGCAAGAAAAGAAACTGGAAGTGTATCAGAGCATTGC<br>GGATCTGGCCGGTGGGTGCGAAAGACCAGGCGGTGTTCAAGTGCGAAGTTAGCGATGAGAAC<br>GTTCGTGGTGTGTGGCTGAAAAACGGCAAGGAGCTGGTTCCGGACAACCGTATCAAAGTGA<br>GCCACATTGGTCGTGTTCACAAGCTGACCATCGACGATGTTACCCGGCGACGAAGCGGA<br>TTATAGCTTCGTGCCGGAGGGCTTTGCGTGCAACCTGAGCGCGAAACTGCACTTCATGGAA<br>GTGAAGATCGACTTTGTTCCGCGTCAGGAGCCGCCGAAAATTCATCTGGATTGCCCGGGTA<br>GCACCCCGGACACCATTGTGGTTGTGGCGGGTAACAAACTGCGTCTGGATGTGCCGATTAG<br>CGGCGACCCGGCGCCGACCGTTGTGTGGCAGAAGACCGTGACCCAAGGTAAGAAAGCGAG<br>CACCGGTCCGCACCCGGATGCGCCGGAGGATGCGGGTGCGGACGAGGAATGGGTTTTCGA<br>TAAGAAACTGCTGTGCGAAACCGAAGGCCGTGTTCGTGTGGAAACCACCAAGGATCGTAGC<br>GTTTTTACCGTGGAGGGCGCGGAGAAAGAAGACGAGGGTGTTTACACCGTTACCGTGAAGA<br>ACCCGGTGGGTGAAGACCAGGTTAACCTGACCGTTAAAGTTATTGATGTTCCGGATGCGCCG<br>GCGGCGCCGAAGATTAGCAACGTGGGTGAAGATAGCTGCACCGTTCAATGGGAGCCGCCG<br>GCGTATGATGGTGGCCAGCCGGTGCTGGGCTATATCCTGGAGCGTAAGAAAAAGAAAAGCT<br>ATCGTTGGATGCGTCTGAACTTCGACCTGCTGCGTGAACTGAGCCACGAGGCGCGTCGTAT<br>GATTGAAGGTGTTGCGTACGAGATGCGTGTTTATGCGGTGAACGCGGTTGGTATGAGCCGT<br>CCGAGCCCGGCGAGCCAGCCGTTTATGCCGATTGGTCCGCCGGGTGAACCGACCCACCTG<br>GCGGTGGAGGACGTTAGCGATACCACCGTGAGCCTGAAATGGCGTCCGCCGGAACGTGTT<br>GGTGCGGGTGGCCTGGATGGCTACAGCGTGGAATATTGCCAAGAGGGCTGCAGCGAATGG<br>ACCCCGGCGCTGCAGGGTCTGACCGAGCGTACCAGCATGCTGGTTAAAGACCTGCCGACC<br>GGTGCGCGTCTGCTGTTCCGTGTGCGTGCGCATAACGTTGCGGGTCCGGGTGGCCCGATC<br>GTGACCAAGGAACCGGTTACCGTGCAGGAGATT[AGCGGTGATAGCGCGACCCACATTAAAT<br>TTAGCAAGCGTGACGAGGATGGTAAAGAACTGGCGGGCGCGACCATGGAACTGCGTGACAG<br>CAGCGGCAAGACCATCAGCACCTGGATTAGCGATGGTCAGGTTAAAGACTTCTACCTGTATC<br>CGGGCAAGTACACCTTTGTGGAAACCGCGGCGCCGGATGGTTATGAGGTGGCGACCGCGA<br>TCACCTTCACCGTTAACGAGCAGGGTCAAGTTACCGTGAACGGTAAAGCGACCAAGGGC][G<br>AGAATCTGTATTTCCAGGGT][CATCACCACCACCATCAC]TAA |
| SEQ ID NO: 3 | ATGCCGGAGCCGGGTAAAAAGCCGGTTAGCGCGTTCAACAAAAAACCGCGTAGCGCGGAAG<br>TGACCGCGGGTAGCGCGGCGGTGTTTGAGGCGGAAACCGAGCGTAGCGGCGTTAAAGTGC<br>GTTGGCAACGTGACGGTAGCGATATTACCGCGAACGATAAATACGGTCTGGCGGCGGAAGG<br>CAAGCGTCACACCCTGACCGTTCGTGATGCGAGCCCGGACGATCAGGGTAGCTATGCGGTG<br>ATCGCGGGCAGCAGCAAGGTGAAATTTGACCTGAAAGTTACCGAGCCGGCTCCGCCGGAAA<br>AAGCGGAAAGCGAGGTGGCGCCGGGTGCGCCGAAGGAAGTTCCGGCGCCGGCGACCGAG<br>CTGGAGGAAAGCGTGAGCAGCCCGGAAGGCAGCGTTAGCGTGACCCAGGATGGTAGCGCG<br>GCGGAACATCAAGGTGCGCCGGATGATCCGATCGGTCTGTTCCTGATGCGTCCGCAAGACG<br>GTGAGGTTACCGTGGGTGGCAGCATTGTGTTTAGCGCGCGTGTTGCGGGTGCGAGCCTGCT<br>GAAACCGCCGGTGGTTAAGTGGTTCAAGGGCAAATGGGTGGATCTGAGCAGCAAAGTTGGT<br>CAGCACCTGCAACTGCACGACAGCTACGATCGTGCGAGCAAGGTTTACCTGTTCGAACTGCA<br>CATTACCGATGCGCAGACCACCAGCGCGGGTGGCTACCGTTGCGAGGTTAGCACCAAGGAC<br>AAATTCGATAGCTGCAACTTTAACCTGACCGTGCACGAAGCGATCGGTAGCGGCGACCTGG<br>ATCTGCGTAGCGCGTTTCGTCGTACCAGCCTGGCGGGTGCGGGTCGTCGTACCAGCGACAG<br>CCATGAGGATGCGGGCACCCTGGATTTCAGCAGCCTGCTGAAGAAACGTGATAGCTTTCGT<br>CGTGACAGCAAACTGGAAGCGCCGGCGGAGGAAGACGTTTGGGAGATCCTGCGTCAAGCT<br>CCGCCGAGCGAATACGAGCGTATTGCGTTCCAGCACGGTGTGACCGATCTGCGTGGCATGC<br>TGAAGCGT[CCG]AAGGGTATGAAGCAGGACGAAAAGAAAAGCACCGCGTTTCAGAAGAAACT<br>GGAGCCGGCGTATCAAGTGAACAAAGGCCACAAGATCCGTCTGACCGTGGAACTGGCGGAC<br>CCGGATGCGGAAGTGAAATGGCTGAAGAACGGCCAGGAAATCCAAATGAGCGGTAGCAAAT<br>ACATTTTCGAGAGCGTTGGTGCGAAGCGTACCCTGACCATTAGCCAATGCAGCCTGGCGGA<br>CGATGCGGCGTATCAGTGCGTGGTTGGTGGCGAGAAATGCAGCACCGAACTGTTCGTGAAG<br>GAGCCGCCGGTTCTGATCACCCGTAGCCTGGAAGATCAGCTGGTTATGGTGGGTCAACGTG<br>TGGAATTTGAGTGCGAAGTTAGCGAGGAAGGCGCGCAAGTGAATTGGCTGAAGGACGGTGT<br>TGAGCTGACCCGTGAGGAAACCTTCAAATACCGTTTTAAGAAAGATGGTCGTAAGCACCACC<br>TGATCATTAACGAAGCGACCCTGGAGGATGCGGGTCACTATGCGGTTCGTACCAGCGGTGG<br>CCAGAGCCTGCGGAACTGATCGTGCAAGAAAAGAAACTGGAAGTGTATCAGAGCATTGCG<br>GATCTGGCCGGTGGGTGCGAAAGACCAGGCGGTGTTCAAGTGCGAAGTTAGCGATGAGAACG<br>TTCGTGGTGTGTGGCTGAAAAACGGCAAGGAGCTGGTTCCGGACAACCGTATCAAAGTGAG |

TABLE 1-continued

| Description | Sequence |
|---|---|
| | CCACATTGGTCGTGTTCACAAGCTGACCATCGACGATGTTACCCCGGCGGACGAAGCGGAT<br>TATAGCTTCGTGCCGGAGGGCTTTGCGTGCAACCTGAGCGCGAAACTGCACTTCATGGAAG<br>TGAAGATCGACTTTGTTCCGCGTCAGGAGCCGCCGAAAATTCATCTGGATTGCCCGGGTAGC<br>ACCCCGGACACCATTGTGGTTGTGGCGGGTAACAAACTGCGTCTGGATGTGCCGATTAGCG<br>GCGACCCGGCGCCGACCGTTGTGTGGCAGAAGACCGTGACCCAAGGTAAGAAAGCGAGCA<br>CCGGTCCGCACCCGGATGCGCCGGAGGATGCGGGTGCGGACGAGGAATGGGTTTTCGATA<br>AGAAACTGCTGTGCGAAACCGAAGGCCGTGTTCGTGTGGAAACCACCAAGGATCGTAGCGT<br>TTTTACCGTGGAGGGCGCGGAGAAAGAAGACGAGGGTGTTTACACCGTTACCGTGAAGAAC<br>CCGGTGGGTGAAGACCAGGTTAACCTGACCGTTAAAGTTATTGATGTTCCGGATGCGCCGG<br>CGGCGCCGAAGATTAGCAACGTGGGTGAAGATAGCTGCACCGTTCAATGGGAGCCGCCGG<br>CGTATGATGGTGGCCAGCCGGTGCTGGGCTATATCCTGGAGCGTAAGAAAAAGAAAAGCTA<br>TCGTTGGATGCGTCTGAACTTCGACCTGCTGCGTGAACTGAGCCACGAGGCGCGTCGTATG<br>ATTGAAGGTGTTGCGTACGAGATGCGTGTTTATGCGGTGAACGCGGTTGGTATGAGCCGTC<br>CGAGCCCGGCGAGCCAGCCGTTTATGCCGATTGGTCCGCCGGGTGAACCGACCCACCTGG<br>CGGTGGAGGACGTTAGCGATACCACCGTGAGCCTGAAATGGCGTCCGCCGGAACGTGTTG<br>GTGCGGGTGGCCTGGATGGCTACAGCGTGGAATATTGCCAAGAGGGCTGCAGCGAATGGA<br>CCCCGGCGCTGCAGGGTCTGACCGAGCGTACCAGCATGCTGGTTAAAGACCTGCCGACCG<br>GTGCGCGTCTGCTGTTCCGTGTGCGTGCGCATAACGTTGCGGGTCCGGGTGGCCCGATCGT<br>GACCAAGGAACCGGTTACCGTGCAGGAGATT[AGCGGTGATAGCGCGACCCACATTAAATTT<br>AGCAAGCGTGACGAGGATGGTAAAGAACTGGCGGGCGCGACCATGGAACTGCGTGACAGC<br>AGCGGCAAGACCATCAGCACCTGGATTAGCGATGGTCAGGTTAAAGACTTCTACCTGTATCC<br>GGGCAAGTACACCTTTGTGGAAACCGCGGCGCCGGATGGTTATGAGGTGGCGACCGCGAT<br>CACCTTCACCGTTAACGAGCAGGGTCAAGTTACCGTGAACGGTAAAGCGACCAAGGGC][GA<br>GAATCTGTATTTCCAGGGT][CATCACCACCACCATCAC]TAA |

Table 4 shows sequences for TEV protease consensus recognition site, SpyCatcher, and cMyBP-C.

TABLE 4

| Description | Sequence |
|---|---|
| SEQ ID NO: 4<br>(Example of TEV<br>Protease<br>recognition<br>site) | GAGAATCTGTATTTCCAGGGT |
| SEQ ID NO: 5<br>(TEV Protease<br>recognition<br>site) | E-Xaa-Xaa-Y-Xaa-Q-G |
| SEQ ID NO: 6<br>(TEV Protease<br>recognition<br>site) | E-Xaa-Xaa-Y-Xaa-Q-S |
| SEQ ID NO: 7<br>(SpyCatcher) | AGCGGTGATAGCGCGACCCACATTAAATTTAGCAAGCGTGACGAGGATGGTAA<br>AGAACTGGCGGGCGCGACCATGGAACTGCGTGACAGCAGCGGCAAGACCATC<br>AGCACCTGGATTAGCGATGGTCAGGTTAAAGACTTCTACCTGTATCCGGGCAA<br>GTACACCTTTGTGGAAACCGCGGCGCCGGATGGTTATGAGGTGGCGACCGCG<br>ATCACCTTCACCGTTAACGAGCAGGGTCAAGTTACCGTGAACGGTAAAGCGAC<br>CAAGGGC |
| SEQ ID NO: 8<br>(SpyCatcher<br>protein) | SGDSATHIKFSKRDEDGKELAGATMELRDSSGKTISTWISDGQVKDFYLYPGKYTF<br>VETAAPDGYEVATAITFTVNEQGQVTVNGKATKG |
| SEQ ID NO: 9<br>(SpyTag<br>protein) | AHIVMVDAYKPTK |
| SEQ ID NO: 10<br>(cMyBP-C<br>protein) | MPEPGKKPVSAFNKKPRSAEVTAGSAAVFEAETERSGVMVRWQRDGSDITANDK<br>YGLAAEGKRHTLTVRDASPDDQGSYAVIAGSSKVKFDLKVTEPAPPEKAESEVAP<br>GAPEEVPAPATELEESVSSPEGSVSVTQDGSAAEHQGAPDDPIGLFLMRPQDGEV<br>TVGGSIVESARVAGASLLKPPVVKWFKGKWVDLSSKVGQHLQLHDSYDRASKVYL<br>FELHITDAQTTSAGGYRCEVSTKDKFDSCNFNLTVHEAIGSGDLDLRSAFRRTSLA<br>GAGRRTSDSHEDAGTPDFSSLLKKRDSFRRDSKLEAPAEEDVWEILRQAPPSEYE<br>RIAFQHGVEACHRPLKRLKGMKQDEKKSTAFQKKLEPAYQVNKGHKIRLTVELAD<br>PDAEVKWLKNGQEIQMSGSKYIFESVGAKRTLTISQCSLADDAAYQCVVGGEKCS<br>TELFVKEPPVLITRSLEDQLVMVGQRVEFECEVSEEGAQVKWLKDGVELTREETF<br>KYRFKKDGRKHHLIINEATLEDAGHYAVRTSGGQSLAELIVQEKKLEVYQSIADLAV<br>GAKDQAVEKCEVSDENVRGVWLKNGKELVPDNRIKVSHIGRVHKLTIDDVTPADE<br>ADYSFVPEGFACNLSAKLHFMEVKIDFVPRQEPPKIHLDCPGSTPDTIVVVTGNKLR |

TABLE 4-continued

| Description | Sequence |
|---|---|
| | LDVPISGDPAPTVVWQKTVTQGKKASAGPHPDAPEDAGADEEWVEDKKLLCETE
GRVRVETTKDRSVFTVEGAEKEDEGVYTVTVKNPVGEDQVNLTVKVIDVPDAPAA
PKISNVGEDSCTVQWEPPAYDGGQPVLGYILERKKKSYRWMRLNEDLLRELSHE
ARRMIEGVAYEMRVYAVNAVGMSRPSPASQPFMPIGPPGEPTHLAVEDVSDTTVS
LKWRPPERVGAGGLDGYSVEYCQEGCSEWTPALQGLTERRSMLVKDLPTGARLL
FRVRAHNVAGPGGPIVTKEPVTVQEILQRPRLQLPRHLRQTIQKKVGEPVNLLIPFQ
GKPRPQVTWTKEGQPLAGEEVSIRNSPTDTILFIRAARRTHSGTYQVIVRIENMED
KATLILQIVDKPSPPQDIRIVETWGFNVALEWKPPQDDGNTEIWGYTVQKADKKTM
EWFTVLEHYRRTHCVVSELIIGNGYYFRVFSHNMVGSSDKAAATKEPVFIPRPGITY
EPPKYKALDFSEAPSFTQPLANRSIIAGYNAILCCAVRGSPKPKISWEKNGLDLGED
ARFRMECKQGVLTLEIRKPCPYDGGVYVCRATNLQGEAQCECRLEVRVPQ |
| SEQ ID NO: 11
(cMyBP-C C0-C7
domains) | ATGCCGGAGCCGGGTAAAAAGCCGGTTAGCGCGTTCAACAAAAAACCGCGTA
GCGCGGAAGTGACCGCGGGTAGCGCGGCGGTGTTTGAGGCGGAAACCGAGC
GTAGCGGCGTTAAAGTGCGTTGGCAACGTGACGGTAGCGATATTACCGCGAA
CGATAAATACGGTCTGGCGGCGGAAGGCAAGCGTCACACCCTGACCGTTCGT
GATGCGAGCCCGGACGATCAGGGTAGCTATGCGGTGATCGCGGGCAGCAGC
AAGGTGAAATTTGACCTGAAAGTTACCGAGCCGGCTCCGCCGGAAAAAGCGG
AAAGCGAGGTGGCGCCGGGTGCGCCGAAGGAAGTTCCGGCGCCGGCGACCG
AGCTGGAGGAAAGCGTGAGCAGCCCGGAAGGCAGCGTTAGCGTGACCCAGG
ATGGTAGCGCGGCGGAACATCAAGGTGCGCCGGATGATCCGATCGGTCTGTT
CCTGATGCGTCCGCAAGACGGTGAGGTTACCGTGGGTGGCAGCATTGTTTTA
GCGCGCGTGTTGCGGGTGCGAGCCTGCTGAAACCGCCGGTGGTTAAGTGGTT
CAAGGGCAAATGGGTGGATCTGAGCAGCAAAGTTGGTCAGCACCTGCAACTG
CACGACAGCTACGATCGTGCGAGCAAGGTTTACCTGTTCGAACTGCACATTAC
CGATGCGCAGACCACCAGCGCGGGTGGCTACCGTTGCGAGGTTAGCACCAAG
GACAAATTCGATAGCTGCAACTTTAACCTGACCGTGCACGAAGCGATCGGTAG
CGGCGACCTGGATCTGCGTAGCGCGTTTCGTCGTACCAGCCTGGCGGGTGCG
GGTCGTCGTACCAGCGACAGCCATGAGGATGCGGGCACCCTGGATTTCAGCA
GCCTGCTGAAGAAACGTGATAGCTTTCGTCGTGACAGCAAACTGGAAGCGCCG
GCGGAGGAAGACGTTTGGGAGATCCTGCGTCAAGCTCCGCCGAGCGAATACG
AGCGTATTGCGTTCCAGCACGGTGTGACCGATCTGCGTGGCATGCTGAAGCG
TCTGAAGGGTATGAAGCAGGACGAAAAGAAAAGCACCGCGTTTCAGAAGAAAC
TGGAGCCGGCGTATCAAGTGAACAAAGGCCACAAGATCCGTCTGACCGTGGA
ACTGGCGGACCCGGATGCGGAAGTGAAATGGCTGAAGAACGGCCAGGAAATC
CAAATGAGCGGTAGCAAATACATTTTCGAGAGCGTTGGTGCGAAGCGTACCCT
GACCATTAGCCAATGCAGCCTGGCGGACGATGCGGCGTATCAGTGCGTGGTT
GGTGGCGAGAAATGCAGCACCGAACTGTTCGTGAAGGAGCCGCCGGTTCTGA
TCACCCGTAGCCTGGAAGATCAGCTGGTTATGGTGGGTCAACGTGTGGAATTT
GAGTGCGAAGTTAGCGAGGAAGGCGCGCAAGTGAAATGGCTGAAGGACGGTG
TTGAGCTGACCCGTGAGGAAACCTTCAAATACCGTTTTAAGAAAGATGGTCGTA
AGCACCACCTGATCATTAACGAAGCGACCCTGGAGGATCGGGTCACTATGC
GGTTCGTACCAGCGGTGGCCAGAGCCTGGCGGAACTGATCGTGCAAGAAAAG
AAACTGGAAGTGTATCAGAGCATTGCGGATCTGGCGGTGGGTGCGAAAGACC
AGGCGGTGTTCAAGTGCGAAGTTAGCGATGAGAACGTTCGTGGTGTGTGGCT
GAAAAACGGCAAGGAGCTGGTTCCGGACAACCGTATCAAGTGAGCCACATTG
GTCGTGTTCACAAGCTGACCATCGACGATGTTACCCCGGCGGACGAAGCGGA
TTATAGCTTCGTGCCGGAGGGCTTTGCGTGCAACCTGAGCGCGAAACTGCACT
TCATGGAAGTGAAGATCGACTTTGTTCCGCGTCAGGAGCCGCCGAAAATTCAT
CTGGATTGCCCGGGTAGCACCCCGGACACCATTGTGGTTGTGGCGGGTAACA
AACTGCGTCTGGATGTGCCGATTAGCGGCGACCCGGCGCCGACCGTTGTGTG
GCAGAAGACCGTGACCCAAGGTAAGAAAGCGAGCACCGGTCCGCACCCGGAT
GCGCCGGAGGATGCGGGTGCGGACGAGGAATGGGTTTTCGATAAGAAACTGC
TGTGCGAAACCGAAGGCCGTGTTCGTGTGGAAACCACCAAGGATCGTAGCGTT
TTTACCGTGGAGGGCGCGGAGAAAGAAGACGAGGGTGTTTACACCGTTACCG
TGAAGAACCCGGTGGGTGAAGACCAGGTTAACCTGACCGTTAAAGTTATTGAT
GTTCCGGATGCGCCGGCGGCGCCGAAGATTAGCAACGTGGGTGAAGATAGCT
GCACCGTTCAATGGGAGCCGCCGGCGTATGATGGTGGCCAGCCGGTGCTGG
GCTATATCCTGGAGCGTAAGAAAAAGAAAAGCTATCGTTGGATGCGTCTGAAC
TTCGACCTGCTGCGTGAACTGAGCCACGAGGCGCGTCGTATGATTGAAGGTGT
TGCGTACGAGATGCGTGTTTATGCGGTGAACGCGGTTGGTATGAGCCGTCCG
AGCCCGGCGAGCCAGCCGTTTATGCCGATTGGTCCGCCGGGTGAACCGACCC
ACCTGGCGGTGGAGGACGTTAGCGATACCACCGTGAGCCTGAAATGGCGTCC
GCCGGAACGTGTTGGTGCGGGTGGCCTGGATGGCTACAGCGTGGAATATTGC
CAAGAGGGCTGCAGCGAATGGACCCCGGCGCTGCAGGGTCTGACCGAGCGT
ACCAGCATGCTGGTTAAAGACCTGCCGACCGGTGCGCGTCTGCTGTTCCGTGT
GCGTGCGCATAACGTTGCGGGTCCGGGTGGCCCGATCGTGACCAAGGAACCG
GTTACCGTGCAGGAGATT |
| SEQ ID NO: 12
(cMyBP-C C0-C7
domains) | MPEPGKKPVSAFNKKPRSAEVTAGSAAVFEAETERSGVKVRWQRDGSDITANDK
YGLAAEGKRHTLTVRDASPODQGSYAVIAGSSKVKFDLKVTEPAPPEKAESEVAP
GAPKEVPAPATELEESVSSPEGSVSVTQDGSAAEHQGAPDDPIGLFLMRPQDGEV
TVGGSIVFSARVAGASLLKPPVVKWFKGKWVDLSSKVGQHLQLHDSYDRASKVYL
FELHITDAQTTSAGGYRCEVSTKDKFDSCNFNLTVHEAIGSGDLDLRSAFRRTSLA
GAGRRTSDSHEDAGTLDFSSLLKKRDSFRRDSKLEAPAEEDVWEILRQAPPSEYE
RIAFQHGVTDLRGMLKRLKGMKQDEKKSTAFQKKLEPAYQVNKGHKIRLTVELAD
PDAEVKWLKNGQEIQMSGSKYIFESVGAKRTLTISQCSLADDAAYQCVVGGEKCS
TELFVKEPPVLITRSLEDQLVMVGQRVEFECEVSEEGAQVKWLKDGVELTREETF |

TABLE 4-continued

| Description | Sequence |
|---|---|
| | KYRFKKDGRKHHLIINEATLEDAGHYAVRTSGGQSLAELIVQEKKLEVYQSIADLAV<br>GAKDQAVEKCEVSDENVRGVWLKNGKELVPDNRIKVSHIGRVHKLTIDDVTPADE<br>ADYSFVPEGFACNLSAKLHFMEVKIDFVPRQEPPKIHLDCPGSTPDTIVVVAGNKL<br>RLDVPISGDPAPTVVWQKTVTQGKKASTGPHPDAPEDAGADEEWVEDKKLLCET<br>EGRVRVETTKDRSVETVEGAEKEDEGVYTVTVKNPVGEDQVNLTVKVIDVPDAPA<br>APKISNVGEDSCTVQWEPPAYDGGQPVLGYILERKKKKSYRWMRLNFDLLRELSH<br>EARRMIEGVAYEMRVYAVNAVGMSRPSPASQPFMPIGPPGEPTHLAVEDVSDTTV<br>SLKWRPPERVGAGGLDGYSVEYCQEGCSEWTPALQGLTERTSMLVKDLPTGARL<br>LERVRAHNVAGPGGPIVTKEPVTVQEI |
| SEQ ID NO: 13<br>(C0-C7-SC-ST-<br>C8-C10) | MPEPGKKPVSAFNKKPRSAEVTAGSAAVFEAETERSGVKVRWQRDGSDITANDK<br>YGLAAEGKRHTLTVRDASPDDQGSYAVIAGSSKVKFDLKVTEPAPPEKAESEVAP<br>GAPKEVPAPATELEESVSSPEGSVSVTQDGSAAEHQGAPDDPIGLFLMRPQDGEV<br>TVGGSIVFSARVAGASLLKPPVVKWFKGKWVDLSSKVGQHLQLHDSYDRASKVYL<br>FELHITDAQTTSAGGYRCEVSTKDKFDSCNFNLTVHEAIGSGDLDLRSAFRRTSLA<br>GAGRRTSDSHEDAGTLDFSSLLKKRDSFRRDSKLEAPAEEDVWEILRQAPPSEYE<br>RIAFQHGVTDLRGMLKRLKGMKQDEKKSTAFQKKLEPAYQVNKGHKIRLTVELAD<br>PDAEVKWLKNGQEIQMSGSKYIFESVGAKRTLTISQCSLADDAAYQCVVGGEKCS<br>TELFVKEPPVLITRSLEDQLVMVGQRVEFECEVSEEGAQVKWLKDGVELTREETF<br>KYRFKKDGRKHHLIINEATLEDAGHYAVRTSGGQSLAELIVQEKKLEVYQSIADLAV<br>GAKDQAVFKCEVSDENVRGVWLKNGKELVPDNRIKVSHIGRVHKLTIDDVTPADE<br>ADYSFVPEGFACNLSAKLHFMEVKIDFVPRQEPPKIHLDCPGSTPDTIVVVAGNKL<br>RLDVPISGDPAPTVVWQKTVTQGKKASTGPHPDAPEDAGADEEWVFDKKLLCET<br>EGRVRVETTKDRSVFTVEGAEKEDEGVYTVTVKNPVGEDQVNLTVKVIDVPDAPA<br>APKISNVGEDSCTVQWEPPAYDGGQPVLGYILERKKKKSYRWMRLNFDLLRELSH<br>EARRMIEGVAYEMRVYAVNAVGMSRPSPASQPFMPIGPPGEPTHLAVEDVSDTTV<br>SLKWRPPERVGAGGLDGYSVEYCQEGCSEWTPALQGLTERTSMLVKDLPTGARL<br>LFRVRAHNVAGPGGPIVTKEPVTVQEISGDSATHIKFSKRDEDGKELAGATMELRD<br>SSGKTISTWISDGQVKDFYLYPGKYTFVETAAPDGYEVATAITFTVNEQGQVTVNG<br>KATKGGAHIVMVDAYKPTKLQRPRLQLPRHLRQTIQKKVGEPVNLLIPFQGKPRPQ<br>VTWTKEGQPLAGEEVSIRNSPTDTILFIRAARRTHSGTYQVTVRIENMEDKATLILQI<br>VDKPSPPQDIRIVETWGFNVALEWKPPQDDGNTEIWGYTVQKADKKTMEWFTVLE<br>HYRRTHCVVSELIIGNGYYFRVFSHNMVGSSDKAAATKEPVFIPRPGITYEPPKYKA<br>LDFSEAPSFTQPLANRSIIAGYNAILCCAVRGSPKPKISWFKNGLDLGEDARFRMFC<br>KQGVLTLEIRKPCPYDGGVYVCRATNLQGEAQCECRLEVRVPQ |

Applications

The methods and/or compositions of present invention may be used as a research tool, for example to study cMyBP-C (e.g., to study its function, its features, drug interactions, mutations that lead to diseases, effects of introduced mutations, effects of post-translational modification such as phosphorylation, effects of a longer or shorter domains, effects of stiffer or more compliant domains, etc.), to study diseases such as hypertrophic cardiomyopathy, or for other research purposes. The present invention may also be applied to other proteins, such as skeletal muscle MyBP-C isoforms or other sarcomere proteins. There is also the potential to develop cell lines (e.g., stem cells) with a cassette (e.g., TEV/SpyTag cassette) in cMyBP-C or other sarcomere proteins.

In certain embodiments the methods and/or compositions of the present invention are used in motility assays. For example, in certain embodiments, recombinant cMyBP-C proteins of the present invention may be used in motility assays to test the effects of certain drugs. In certain embodiments, recombinant cMyBP-C proteins of the present invention may be used in motility assays for the purpose of evaluating the effects of mutations or changes in the cMyBP-C protein. The present invention is not limited to these uses for the recombinant cMyBP-C proteins or purposes of motility assays. Standard motility assays have coverslipped slides with attached myosin heads (se FIG. 4), wherein the attached myosin heads can propel fluorescently labeled filaments of actin. The recombinant cMyBP-C proteins of the present invention would be more suitable for motility assays that feature isolated thick filaments linked to a coverslip (see FIG. 5), which allow myosin heads to be in a configuration that is more physiologically relevant and allow for the appropriate positioning and function of cMyBP-C.

Thick filaments for use in such assays can be isolated from systems expressing recombinant cMyBP-C proteins that are constructed using methods of the present invention (e.g., the thick filaments can be isolated from Spy-C mice, from permeabilized myocytes, etc.). These isolated thick filaments can be attached to a coverslip as demonstrated in Previs et al. (Science 2012, 337:1215-1218), and the filaments can be used to test the effects of particular drug (e.g., to see if the drug is an activator or an inhibitor, etc.). In certain embodiments, the filaments featuring recombinant cMyBP-C proteins are used for research purposes, e.g., to evaluate the function or effects of mutations or changes to the cMyBP-C protein. In certain embodiments, force measurements may be used to assess the results of a drug screen or to test the effects of mutations or changes to the cMyBP-C protein. In certain embodiments, the speed of the actin molecules may be assessed to determine the results of a drug screen or to test the effects of mutations or changes to the cMyBP-C protein.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A recombinant protein comprising cMyBP-C with an internal insertion therein, the internal insertion comprises at least a SpyTag peptide adjacent to a protease recognition site, wherein the internal insertion is within or between C7 and C8 domains of cMyBP-C.

2. A recombinant protein comprising cMyBP-C with an internal insertion therein, the internal insertion comprises at least a SpyTag peptide adjacent to a protease recognition site, wherein the internal insertion is in between residues VQEILQR (SEQ ID NO: 14) in domain C7 and residues PRLQLPRH (SEQ ID NO: 15) of domain C8 of cMyBP-C.

3. A recombinant protein comprising cMyBP-C with an internal insertion therein, wherein the recombinant cMyBP-C peptide is according to SEQ ID NO: 13.

4. A method of producing a recombinant cMyBP-C protein, said method comprising:
   a. introducing into a genome of a host a cassette for expressing a first recombinant cMyBP-C protein, wherein the first recombinant protein is according to the recombinant protein of claim 1, wherein the protease recognition site is adjacent to and 5' to the SpyTag peptide;
   b. isolating myocytes from the host;
   c. introducing to the myocytes a protease that cleaves the first cMyBP-C protein at the protease recognition site to remove its N-terminus and expose the SpyTag peptide;
   d. introducing a recombinant cMyBP-C N-terminus, the recombinant cMyBP-C N-terminus being at least a portion of cMyBP-C with a SpyCatcher peptide at its C-terminus;
      wherein the SpyCatcher peptide of the cMyBP-C N-terminus binds to the SpyTag peptide of the first recombinant cMyBP-C to produce a second recombinant cMyBP-C protein.

5. A motility assay platform comprising: a coverslip with a thick filament disposed thereon, wherein the thick filament comprises a recombinant cMyBP-C protein according to claim 1.

6. A method of producing a recombinant cMyBP-C protein, said method comprising:
   a. introducing into a genome of a host a cassette for expressing a first recombinant cMyBP-C protein, wherein the first recombinant protein is according to the recombinant protein of claim 2, wherein the protease recognition site is adjacent to and 5' to the SpyTag peptide;
   b. isolating myocytes from the host;
   c. introducing to the myocytes a protease that cleaves the first cMyBP-C protein at the protease recognition site to remove its N-terminus and expose the SpyTag peptide;
   d. introducing a recombinant cMyBP-C N-terminus, the recombinant cMyBP-C N-terminus being at least a portion of cMyBP-C with a SpyCatcher peptide at its C-terminus;

wherein the SpyCatcher peptide of the cMyBP-C N-terminus binds to the SpyTag peptide of the first recombinant cMyBP-C to produce a second recombinant cMyBP-C protein.

7. A motility assay platform comprising: a coverslip with a thick filament disposed thereon, wherein the thick filament comprises a recombinant cMyBP-C protein according to claim 2.

8. A method of producing a recombinant cMyBP-C protein, said method comprising:
   a. introducing into a genome of a host a cassette for expressing a first recombinant cMyBP-C protein, the first recombinant cMyBP-C protein being a cMyBP-C peptide with an internal insertion therein, the internal insertion comprising a protease recognition site adjacent to and 5' to a SpyTag peptide, wherein the internal insertion is within or between C7 and C8 domains of cMyBP-C;
   b. isolating myocytes from the host;
   c. introducing to the myocytes a protease that cleaves the first cMyBP-C protein at the protease recognition site to remove its N-terminus and expose the SpyTag peptide;
   d. introducing a recombinant cMyBP-C N-terminus, the recombinant cMyBP-C N-terminus being at least a portion of cMyBP-C with a SpyCatcher peptide at its C-terminus;
      wherein the SpyCatcher peptide of the cMyBP-C N-terminus binds to the SpyTag peptide of the first recombinant cMyBP-C to produce a second recombinant cMyBP-C protein according to claim 3.

9. A motility assay platform comprising: a coverslip with a thick filament disposed thereon, wherein the thick filament comprises a recombinant cMyBP-C protein according to claim 3.

* * * * *

SEQUENCE LISTING

```
<160> NUMBER OF SEQ ID NOS: 15

<210> SEQ ID NO 1
<211> LENGTH: 3201
<212> TYPE: DNA
<213> ORGANISM: Artificial Sequence
<220> FEATURE:
<223> OTHER INFORMATION: wild-type cMyBP-C C0-C7 domains with SpyCatcher
      followed by a TEV recognition site, His Tag, and Stop codon
<220> FEATURE:
<221> NAME/KEY: misc_feature
<222> LOCATION: (2890)..(3159)
<223> OTHER INFORMATION: SpyCatcher sequence
<220> FEATURE:
<221> NAME/KEY: misc_feature
<222> LOCATION: (3160)..(3180)
<223> OTHER INFORMATION: TEV protease recognition site
<220> FEATURE:
<221> NAME/KEY: misc_feature
<222> LOCATION: (3181)..(3189)
<223> OTHER INFORMATION: His tag

<400> SEQUENCE: 1
atgccggagc cgggtaaaaa gccggttagc gcgttcaaca aaaaaccgcg tagcgcggaa      60
gtgaccgcgg gtagcgcggc ggtgtttgag gcggaaaccg agcgtagcgg cgttaaagtg     120
cgttggcaac gtgacggtag cgatattacc gcgaacgata aatacggtct ggcggcggaa     180
ggcaagcgtc acaccctgac cgttcgtgat gcgagcccgg acgatcaggg tagctatgcg     240
gtgatcgcgg gcagcagcaa ggtgaaattt gacctgaaag ttaccgagcc ggctccgccg     300
gaaaaagcgg aaagcgaggt ggcgccgggt gcgccgaagg aagttccggc gccggcgacc     360
gagctggagg aaagcgtgag cagcccggaa ggcagcgtta gcgtgaccca ggatggtagc     420
gcggcggaac atcaaggtgc gccggatgat ccgatcggtc tgttcctgat gcgtccgcaa     480
gacggtgagg ttaccgtggg tggcagcatt gtgtttagcg cgcgtgttgc gggtgcgagc     540
ctgctgaaac cgccggtggt taagtggttc aagggcaaat gggtggatct gagcagcaaa     600
gttggtcagc acctgcaact gcacgacagc tacgatcgtg cgagcaaggt ttacctgttc     660
gaactgcaca ttaccgatgc gcagaccacc agcgcgggtg gctaccgttg cgaggttagc     720
accaaggaca aattcgatag ctgcaacttt aacctgaccg tgcacgaagc gatcggtagc     780
ggcgacctgg atctgcgtag cgcgtttcgt cgtaccagcc tggcgggtgc gggtcgtcgt     840
accagcgaca gccatgagga tgcgggcacc ctggatttca gcagcctgct gaagaaacgt     900
gatagctttc gtcgtgacag caaactggaa gcgccggcg aggaagacgt ttgggagatc     960
ctgcgtcaag ctccgccgag cgaatacgag cgtattgcgt tccagcacgg tgtgaccgat    1020
ctgcgtggca tgctgaagcg tctgaagggt atgaagcagg acgaaaagaa agcaccgcg    1080 tttcagaaga actggagcc ggcgtatcaa gtgaacaaag ccacaagat ccgtctgacc     1140 gtggaactgg cggacccgga tgcggaagtg aaatggctga gaacggcca ggaaatccaa    1200 atgagcggta gcaaatacat tttcgagagc gttggtgcga agcgtaccct gaccattagc    1260
```

```
caatgcagcc tggcggacga tgcggcgtat cagtgcgtgg ttggtggcga gaaatgcagc    1320
accgaactgt tcgtgaagga gccgccggtt ctgatcaccc gtagcctgga agatcagctg    1380
gttatggtgg gtcaacgtgt ggaatttgag tgcgaagtta gcgaggaagg cgcgcaagtg    1440
aaatggctga aggacggtgt tgagctgacc cgtgaggaaa ccttcaaata ccgttttaag    1500
aaagatggtc gtaagcacca cctgatcatt aacgaagcga ccctggagga tgcgggtcac    1560
tatgcggttc gtaccagcgg tggccagagc ctggcgaaac tgatcgtgca agaaaagaaa    1620
ctggaagtgt atcagagcat tgcggatctg cggtgggtg cgaaagacca ggcggtgttc    1680
aagtgcgaag ttagcgatga gaacgttcgt ggtgtgtggc tgaaaaacgg caaggagctg    1740
gttccggaca accgtatcaa agtgagccac attggtcgtg ttcacaagct gaccatcgac    1800
gatgttaccc cggcgacga gcggattat agcttcgtgc cggagggctt tgcgtgcaac    1860
ctgagcgcga aactgcactt catggaagtg aagatcgact ttgttccgcg tcaggagccg    1920
ccgaaaattc atctggattg cccgggtagc accccggaca ccattgtggt tgtggcgggt    1980
aacaaactgc gtctggatgt gccgattagc ggcgacccgg cgccgaccgt tgtgtggcag    2040
aagaccgtga cccaaggtaa gaaagcgagc accggtccgc acccggatgc gccggaggat    2100
gcgggtgcgg acgaggaatg ggttttcgat aagaaactgc tgtgcgaaac cgaaggccgt    2160
gttcgtgtgg aaaccaccaa ggatcgtagc gttttaccg tggagggcgc ggagaaagaa    2220
gacgagggtg tttacaccgt taccgtgaag aacccggtgg gtgaagacca ggttaacctg    2280
accgttaaag ttattgatgt tccggatgcg ccggcggcgc cgaagattag caacgtgggt    2340
gaagatagct gcaccgttca atgggagccg ccggcgtatg atggtggcca gccggtgctg    2400
ggctatatcc tggagcgtaa gaaaaagaaa agctatcgtt ggatgcgtct gaacttcgac    2460
ctgctgcgtg aactgagcca cgaggcgcgt cgtatgattg aaggtgttgc gtacgagatg    2520
cgtgtttatg cggtgaacgc ggttggtatg agccgtccga gccggcgag ccagccgttt    2580 atgccgattg tccgccggg tgaaccgacc cacctggcgg tggaggacgt tagcgatacc    2640
accgtgagcc tgaaatggcg tccgccggaa cgtgttggtg cgggtggcct ggatggctac    2700
agcgtggaat attgccaaga gggctgcagc gaatggaccc cggcgctgca gggtctgacc    2760
gagcgtacca gcatgctggt taaagacctg ccgaccggtg cgcgtctgct gttccgtgtg    2820
cgtgcgcata cgttgcgggt tccgggtggc ccgatcgtga ccaaggaacc ggttaccgtg    2880
caggagatta gcggtgatag cgcgacccac attaaattta gcaagcgtga cgaggatggt    2940
aaagaactgg cgggcgcgac catggaactg cgtgacagca gcggcaagac catcagcacc    3000
tggattagcg atggtcaggt taaagacttc tacctgtatc cgggcaagta cacctttgtg    3060
gaaaccgcgg cgccggatgg ttatgaggtg gcgaccgcga tcaccttcac cgttaacgag    3120
cagggtcaag ttaccgtgaa cggtaaagcg accaagggcg agaatctgta tttccagggt    3180
catcaccacc accatcacta a                                                3201
```

<210> SEQ ID NO 2
<211> LENGTH: 3201
<212> TYPE: DNA
<213> ORGANISM: Artificial Sequence
<220> FEATURE:
<223> OTHER INFORMATION: cMyBP-C C0-C7 domains containing the [E330K] mutation with SpyCatcher followed by a TEV recognition site, His Tag, and Stop codon
<220> FEATURE:
<221> NAME/KEY: misc_feature
<222> LOCATION: (978)..(980)
<223> OTHER INFORMATION: E330K mutation (compared to wild type cMyBP-C)

```
<220> FEATURE:
<221> NAME/KEY: misc_feature
<222> LOCATION: (2890)..(3159)
<223> OTHER INFORMATION: SpyCatcher sequence
<220> FEATURE:
<221> NAME/KEY: misc_feature
<222> LOCATION: (3160)..(3180)
<223> OTHER INFORMATION: TEV protease recognition site
<220> FEATURE:
<221> NAME/KEY: misc_feature
<222> LOCATION: (3181)..(3198)
<223> OTHER INFORMATION: His tag

<400> SEQUENCE: 2
```

| | | | | | |
|---|---|---|---|---|---|
| atgccggagc | cgggtaaaaa | gccggttagc | gcgttcaaca | aaaaaccgcg | tagcgcggaa | 60 |
| gtgaccgcgg | gtagcgcggc | ggtgtttgag | gcggaaaccg | agcgtagcgg | cgttaaagtg | 120 |
| cgttggcaac | gtgacggtag | cgatattacc | gcgaacgata | atacggtct | ggcggcggaa | 180 |
| ggcaagcgtc | acaccctgac | cgttcgtgat | gcgagcccgg | acgatcaggg | tagctatgcg | 240 |
| gtgatcgcgg | gcagcagcaa | ggtgaaattt | gacctgaaag | ttaccgagcc | ggctccgccg | 300 |
| gaaaaagcgg | aaagcgaggt | ggcgccgggt | gcgccgaagg | aagttccggc | gccggcgacc | 360 |
| gagctggagg | aaagcgtgag | cagcccggaa | ggcagcgtta | gcgtgaccca | ggatggtagc | 420 |
| gcggcggaac | atcaaggtgc | gccggatgat | ccgatcggtc | tgttcctgat | gcgtccgcaa | 480 |
| gacggtgagg | ttaccgtggg | tggcagcatt | gtgtttagcg | cgcgtgttgc | gggtgcgagc | 540 |
| ctgctgaaaa | cgccggtggt | taagtggttc | aagggcaaat | gggtggatct | gagcagcaaa | 600 |
| gttggtcagc | acctgcaact | gcacgacagc | tacgatcgtg | cgagcaaggt | ttacctgttc | 660 |
| gaactgcaca | ttaccgatgc | gcagaccacc | agcgcgggtg | gctaccgttg | cgaggttagc | 720 |
| accaaggaca | aattcgatag | ctgcaacttt | aacctgaccg | tgcacgaagc | gatcggtagc | 780 |
| ggcgacctgg | atctgcgtag | cgcgtttcgt | cgtaccagcc | tggcgggtgc | gggtcgtcgt | 840 |
| accagcgaca | gccatgagga | tgcgggcacc | ctggatttca | gcagcctgct | gaagaaacgt | 900 |
| gatagctttc | gtcgtgacag | caaactggaa | gcgccggcgg | aggaagacgt | ttgggagatc | 960 |
| ctgcgtcaag | ctccgccaag | cgaatacgag | cgtattgcgt | tccagcacgg | tgtgaccgat | 1020 |
| ctgcgtggca | tgctgaagcg | tctgaagggt | atgaagcagg | acgaaaagaa | agcaccgcg | 1080 |
| tttcagaaga | aactggagcc | ggcgtatcaa | gtgaacaaag | gccacaagat | ccgtctgacc | 1140 |
| gtggaactgg | cggaccccgga | tgcggaagtg | aaatggctga | agaacggcca | ggaaatccaa | 1200 |
| atgagcggta | gcaaatacat | tttcgagagc | gttggtgcga | agcgtaccct | gaccattagc | 1260 |
| caatgcagcc | tggcggacga | tgcggcgtat | cagtgcgtgg | ttggtggcga | gaaatgcagc | 1320 |
| accgaactgt | tcgtgaagga | gccgccggtt | ctgatcaccc | gtagcctgga | agatcagctg | 1380 |
| gttatggtgg | gtcaacgtgt | ggaatttgag | tgcgaagtta | gcgaggaagg | cgcgcaagtg | 1440 |
| aaatggctga | aggacggtgt | tgagctgacc | cgtgaggaaa | ccttcaaata | ccgttttaag | 1500 |
| aaagatggtc | gtaagcacca | cctgatcatt | aacgaagcga | ccctgaggga | tgcgggtcac | 1560 |
| tatgcggttc | gtaccagcgg | tggccagagc | ctggcggaac | tgatcgtgca | agaaaagaaa | 1620 |
| ctggaagtgt | atcagagcat | tgcggatctg | gcggtgggtg | cgaaagacca | ggcggtgttc | 1680 |
| aagtgcgaag | ttagcgatga | aacgttcgt | ggtgtgtggc | tgaaaacggg | caaggagctg | 1740 |
| gttccggaca | accgtatcaa | agtgagccac | attggtcgtg | ttcacaagct | gaccatcgac | 1800 |
| gatgttaccc | cggcggacga | agcggattat | agcttcgtgc | cggagggctt | tgcgtgcaac | 1860 |
| ctgagcgcga | aactgcactt | catggaagtg | aagatcgact | ttgttccgcg | tcaggagccg | 1920 |

```
ccgaaaattc atctggattg cccgggtagc accccggaca ccattgtggt tgtggcgggt    1980
aacaaactgc gtctggatgt gccgattagc ggcgacccgg cgccgaccgt tgtgtggcag    2040
aagaccgtga cccaaggtaa gaaagcgagc accggtccgc acccggatgc gccggaggat    2100
gcgggtgcgg acgaggaatg ggttttcgat aagaaactgc tgtgcgaaac cgaaggccgt    2160
gttcgtgtgg aaaccaccaa ggatcgtagc gtttttaccg tggagggcgc ggagaaagaa    2220
gacgagggtg tttacaccgt taccgtgaag aacccggtgg gtgaagacca ggttaacctg    2280
accgttaaag ttattgatgt tccggatgcg ccggcggcgc cgaagattag caacgtgggt    2340
gaagatagct gcaccgttca atgggagccg ccggcgtatg atggtggcca gccggtgctg    2400
ggctatatcc tggagcgtaa gaaaaagaaa agctatcgtt ggatgcgtct gaacttcgac    2460
ctgctgcgtg aactgagcca cgaggcgcgt cgtatgattg aaggtgttgc gtacgagatg    2520
cgtgtttatg cggtgaacgc ggttggtatg agccgtccga gcccggcgag ccagccgttt    2580
atgccgattg gtccgccggg tgaaccgacc cacctggcgg tggaggacgt tagcgatacc    2640
accgtgagcc tgaaatggcg tccgccggaa cgtgttggtg cgggtggcct ggatggctac    2700
agcgtggaat attgccaaga gggctgcagc gaatggaccc cggcgctgca gggtctgacc    2760
gagcgtacca gcatgctggt taaagacctg ccgaccggtg cgcgtctgct gttccgtgtg    2820
cgtgcgcata acgttgcggg tccgggtggc ccgatcgtga ccaaggaacc ggttaccgtg    2880
caggagatta gcggtgatag cgcgacccac attaaattta gcaagcgtga cgaggatggt    2940
aaagaactgg cgggcgcgac catggaactg cgtgacagca gcggcaagac catcagcacc    3000
tggattagcg atggtcaggt taaagacttc tacctgtatc cgggcaagta cacctttgtg    3060
gaaccgcgcg gcgccggatg gttatgaggtg gcgaccgcga tcaccttcac cgttaacgag    3120
cagggtcaag ttaccgtgaa cggtaaagcg accaagggcg agaatctgta tttccagggt    3180
catcaccacc accatcacta a                                               3201
```

<210> SEQ ID NO 3
<211> LENGTH: 3201
<212> TYPE: DNA
<213> ORGANISM: Artificial Sequence
<220> FEATURE:
<223> OTHER INFORMATION: cMyBP-C C0-C7 domains containing the [L348P] mutation with SpyCatcher followed by a TEV recognition site, His Tag, and Stop codon
<220> FEATURE:
<221> NAME/KEY: misc_feature
<222> LOCATION: (1042)..(1044)
<223> OTHER INFORMATION: L348P mutation compared to wild type cMyBP-c protein
<220> FEATURE:
<221> NAME/KEY: misc_feature
<222> LOCATION: (2890)..(3159)
<223> OTHER INFORMATION: Spycatcher sequence
<220> FEATURE:
<221> NAME/KEY: misc_feature
<222> LOCATION: (3160)..(3180)
<223> OTHER INFORMATION: TEV protease recognition site
<220> FEATURE:
<221> NAME/KEY: misc_feature
<222> LOCATION: (3181)..(3198)
<223> OTHER INFORMATION: His tag

<400> SEQUENCE: 3

```
atgccggagc cgggtaaaaa gccggttagc gcgttcaaca aaaaaccgcg tagcgcggaa     60
gtgaccgcgg gtagcgcggc ggtgtttgag gcggaaaccg agcgtagcgg cgttaaagtg    120
cgttggcaac gtgacggtag cgatattacc gcgaacgata aatacggtct ggcggcggaa    180
```

-continued

```
ggcaagcgtc acaccctgac cgttcgtgat gcgagcccgg acgatcaggg tagctatgcg    240
gtgatcgcgg gcagcagcaa ggtgaaattt gacctgaaag ttaccgagcc ggctccgccg    300
gaaaaagcgg aaagcgaggt ggcgccgggt gcgccgaagg aagttccggc gccggcgacc    360
gagctggagg aaagcgtgag cagcccggaa ggcagcgtta gcgtgaccca ggatggtagc    420
gcggcggaac atcaaggtgc gccggatgat ccgatcggtc tgttcctgat gcgtccgcaa    480
gacggtgagg ttaccgtggg tggcagcatt gtgtttagcg cgcgtgttgc gggtgcgagc    540
ctgctgaaac cgccggtggt taagtggttc aagggcaaat gggtggatct gagcagcaaa    600
gttggtcagc acctgcaact gcacgacagc tacgatcgtg cgagcaaggt ttacctgttc    660
gaactgcaca ttaccgatgc gcagaccacc agcgcgggtg gctaccgttg cgaggttagc    720
accaaggaca aattcgatag ctgcaacttt aacctgaccg tgcacgaagc gatcggtagc    780
ggcgacctgg atctgcgtag cgcgtttcgt cgtaccagcc tggcgggtgc gggtcgtcgt    840
accagcgaca gccatgagga tgcgggcacc ctggatttca gcagcctgct gaagaaacgt    900
gatagctttc gtcgtgacag caaactggaa gcgccggcgg aggaagacgt ttgggagatc    960
ctgcgtcaag ctccgccgag cgaatacgag cgtattgcgt ccagcacgg tgtgaccgat    1020 ctgcgtggca tgctgaagcg tccgaagggt atgaagcagg acgaaaagaa aagcaccgcg    1080
tttcagaaga actggagcc ggcgtatcaa gtgaacaaag gccacaagat ccgtctgacc    1140
gtggaactgg cggacccgga tgcggaagtg aaatggctga agaacggcca ggaaatccaa    1200
atgagcggta gcaaatacat tttcgagagc gttggtgcga agcgtaccct gaccattagc    1260
caatgcagcc tggcggacga tgcggcgtat cagtgcgtgg ttggtggcga gaaatgcagc    1320
accgaactgt tcgtgaagga gccgccggtt ctgatcaccc gtagcctgga agatcagctg    1380
gttatggtgg gtcaacgtgt ggaatttgag tgcgaagtta gcgaggaagg cgcgcaagtg    1440
aaatggctga aggacggtgt tgagctgacc cgtgaggaaa ccttcaaata ccgttttaag    1500
aaagatggtc gtaagcacca cctgatcatt aacgaagcga ccctggagga tgcgggtcac    1560
tatgcggttc gtaccagcgg tggccagagc ctggcggaac tgatcgtgca agaaaagaaa    1620
ctggaagtgt atcagagcat tgcggatctg gcggtgggtg cgaaagacca ggcggtgttc    1680
aagtgcgaag ttagcgatga gaacgttcgt ggtgtgtggc tgaaaaacgg caaggagctg    1740
gttccggaca accgtatcaa agtgagccac attggtcgtg ttcacaagct gaccatcgac    1800
gatgttaccc cggcggacga agcggattat agcttcgtgc cggagggctt tgcgtgcaac    1860
ctgagcgcga aactgcactt catggaagtg aagatcgact ttgttccgcg tcaggagccg    1920
ccgaaaattc atctggattg cccgggtagc accccggaca ccattgtggt tgtggcgggt    1980
aacaaactgc gtctggatgt gccgattagc ggcgacccgg cgccgaccgt tgtgtggcag    2040
aagaccgtga cccaaggtaa gaaagcgagc accggtccgc acccggatgc gccggaggat    2100
gcgggtgcgg acgaggaatg ggttttcgat aagaaactgc tgtgcgaaac cgaaggccgt    2160
gttcgtgtgg aaaccaccaa ggatcgtagc gttttttaccg tggagggcgc ggagaaagaa    2220
gacgagggtg tttacaccgt taccgtgaag aacccggtgg gtgaagacca ggttaacctg    2280
accgttaaag ttattgatgt tccggatgcg cggcggcgc cgaagattag caacgtgggt    2340
gaagatagct gcaccgttca atgggagccg ccggcgtatg atggtggcca gccggtgctg    2400
ggctatatcc tggagcgtaa gaaaaagaaa agctatcgtt ggatgcgtct gaacttcgac    2460
ctgctgcgta aactgagcca cgaggcgcgt cgtatgattg aaggtgttgc gtacgagatg    2520
cgtgtttatg cggtgaacgc ggttggtatg agccgtccga gcccggcgag ccagccgttt    2580
```

```
atgccgattg gtccgccggg tgaaccgacc cacctggcgg tggaggacgt tagcgatacc   2640
accgtgagcc tgaaatggcg tccgccggaa cgtgttggtg cgggtggcct ggatggctac   2700
agcgtggaat attgccaaga gggctgcagc gaatggaccc cggcgctgca gggtctgacc   2760
gagcgtacca gcatgctggt taaagacctg ccgaccggtg cgcgtctgct gttccgtgtg   2820
cgtgcgcata acgttgcggg tccgggtggc ccgatcgtga ccaaggaacc ggttaccgtg   2880
caggagatta gcggtgatag cgcgacccac attaaattta gcaagcgtga cgaggatggt   2940
aaagaactgg cgggcgcgac catggaactg cgtgacagca gcggcaagac catcagcacc   3000
tggattagcg atggtcaggt taaagacttc tacctgtatc cgggcaagta cacctttgtg   3060
gaaaccgcgg cgccggatgg ttatgaggtg gcgaccgcga tcaccttcac cgttaacgag   3120
cagggtcaag ttaccgtgaa cggtaaagcg accaagggcg agaatctgta tttccagggt   3180
catcaccacc accatcacta a                                            3201
```

<210> SEQ ID NO 4
<211> LENGTH: 21
<212> TYPE: DNA
<213> ORGANISM: Artificial Sequence
<220> FEATURE:
<223> OTHER INFORMATION: TEV protease recognition site

<400> SEQUENCE: 4
gagaatctgt atttccaggg t                                            21

<210> SEQ ID NO 5
<211> LENGTH: 7
<212> TYPE: PRT
<213> ORGANISM: Artificial Sequence
<220> FEATURE:
<223> OTHER INFORMATION: TEV protease recognition site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 5

Glu Xaa Xaa Tyr Xaa Gln Gly
1               5

<210> SEQ ID NO 6
<211> LENGTH: 7
<212> TYPE: PRT
<213> ORGANISM: Artificial Sequence
<220> FEATURE:
<223> OTHER INFORMATION: TEV protease recognition site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 6

Glu Xaa Xaa Tyr Xaa Gln Ser
1               5

<210> SEQ ID NO 7

```
<211> LENGTH: 270
<212> TYPE: DNA
<213> ORGANISM: Artificial Sequence
<220> FEATURE:
<223> OTHER INFORMATION: SpyCatcher sequence

<400> SEQUENCE: 7
agcggtgata gcgcgaccca cattaaattt agcaagcgtg acgaggatgg taaagaactg     60
gcgggcgcga ccatggaact gcgtgacagc agcggcaaga ccatcagcac ctggattagc    120
gatggtcagg ttaaagactt ctacctgtat ccgggcaagt acacctttgt ggaaaccgcg    180
gcgccggatg gttatgaggt ggcgaccgcg atcaccttca ccgttaacga gcagggtcaa    240
gttaccgtga acggtaaagc gaccaagggc                                     270

<210> SEQ ID NO 8
<211> LENGTH: 90
<212> TYPE: PRT
<213> ORGANISM: Artificial Sequence
<220> FEATURE:
<223> OTHER INFORMATION: SpyCatcher sequence

<400> SEQUENCE: 8

Ser Gly Asp Ser Ala Thr His Ile Lys Phe Ser Lys Arg Asp Glu Asp
1               5                   10                  15

Gly Lys Glu Leu Ala Gly Ala Thr Met Glu Leu Arg Asp Ser Ser Gly
            20                  25                  30

Lys Thr Ile Ser Thr Trp Ile Ser Asp Gly Gln Val Lys Asp Phe Tyr
        35                  40                  45

Leu Tyr Pro Gly Lys Tyr Thr Phe Val Glu Thr Ala Ala Pro Asp Gly
    50                  55                  60

Tyr Glu Val Ala Thr Ala Ile Thr Phe Thr Val Asn Glu Gln Gly Gln
65                  70                  75                  80

Val Thr Val Asn Gly Lys Ala Thr Lys Gly
                85                  90

<210> SEQ ID NO 9
<211> LENGTH: 13
<212> TYPE: PRT
<213> ORGANISM: Artificial Sequence
<220> FEATURE:
<223> OTHER INFORMATION: SpyTag sequence

<400> SEQUENCE: 9

Ala His Ile Val Met Val Asp Ala Tyr Lys Pro Thr Lys
1               5                   10

<210> SEQ ID NO 10
<211> LENGTH: 1270
<212> TYPE: PRT
<213> ORGANISM: Mus musculus

<400> SEQUENCE: 10

Met Pro Glu Pro Gly Lys Lys Pro Val Ser Ala Phe Asn Lys Lys Pro
1               5                   10                  15

Arg Ser Ala Glu Val Thr Ala Gly Ser Ala Val Phe Glu Ala Glu
            20                  25                  30

Thr Glu Arg Ser Gly Val Met Val Arg Trp Gln Arg Asp Gly Ser Asp
        35                  40                  45

Ile Thr Ala Asn Asp Lys Tyr Gly Leu Ala Ala Glu Gly Lys Arg His
    50                  55                  60
```

```
Thr Leu Thr Val Arg Asp Ala Ser Pro Asp Asp Gln Gly Ser Tyr Ala
 65                  70                  75                  80

Val Ile Ala Gly Ser Ser Lys Val Lys Phe Asp Leu Lys Val Thr Glu
                 85                  90                  95

Pro Ala Pro Pro Glu Lys Ala Glu Ser Glu Val Ala Pro Gly Ala Pro
            100                 105                 110

Glu Glu Val Pro Ala Pro Ala Thr Glu Leu Glu Ser Val Ser Ser
        115                 120                 125

Pro Glu Gly Ser Val Ser Val Thr Gln Asp Gly Ser Ala Ala Glu His
    130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
                180                 185                 190

Lys Trp Val Asp Leu Ser Ser Lys Val Gly Gln His Leu Gln Leu His
                195                 200                 205

Asp Ser Tyr Asp Arg Ala Ser Lys Val Tyr Leu Phe Glu Leu His Ile
    210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Asn Phe Asn Leu Thr Val His Glu
                245                 250                 255

Ala Ile Gly Ser Gly Asp Leu Asp Leu Arg Ser Ala Phe Arg Arg Thr
                260                 265                 270

Ser Leu Ala Gly Ala Gly Arg Arg Thr Ser Asp Ser His Glu Asp Ala
    275                 280                 285

Gly Thr Pro Asp Phe Ser Ser Leu Leu Lys Lys Arg Asp Ser Phe Arg
    290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                325                 330                 335

Gly Val Glu Ala Cys His Arg Pro Leu Lys Arg Leu Lys Gly Met Lys
                340                 345                 350

Gln Asp Glu Lys Lys Ser Thr Ala Phe Gln Lys Lys Leu Glu Pro Ala
    355                 360                 365

Tyr Gln Val Asn Lys Gly His Lys Ile Arg Leu Thr Val Glu Leu Ala
    370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Ala Ala Tyr Gln Cys
                420                 425                 430

Val Val Gly Gly Glu Lys Cys Ser Thr Glu Leu Phe Val Lys Glu Pro
            435                 440                 445

Pro Val Leu Ile Thr Arg Ser Leu Glu Asp Gln Leu Val Met Val Gly
        450                 455                 460

Gln Arg Val Glu Phe Glu Cys Glu Val Ser Glu Glu Gly Ala Gln Val
465                 470                 475                 480

Lys Trp Leu Lys Asp Gly Val Glu Leu Thr Arg Glu Glu Thr Phe Lys
```

```
                    485                 490                 495
Tyr Arg Phe Lys Lys Asp Gly Arg Lys His His Leu Ile Ile Asn Glu
                500                 505                 510

Ala Thr Leu Glu Asp Ala Gly His Tyr Ala Val Arg Thr Ser Gly Gly
            515                 520                 525

Gln Ser Leu Ala Glu Leu Ile Val Gln Glu Lys Lys Leu Glu Val Tyr
            530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                565                 570                 575

Gly Lys Glu Leu Val Pro Asp Asn Arg Ile Lys Val Ser His Ile Gly
            580                 585                 590

Arg Val His Lys Leu Thr Ile Asp Asp Val Thr Pro Ala Asp Glu Ala
            595                 600                 605

Asp Tyr Ser Phe Val Pro Glu Gly Phe Ala Cys Asn Leu Ser Ala Lys
            610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
                645                 650                 655

Val Val Thr Gly Asn Lys Leu Arg Leu Asp Val Pro Ile Ser Gly Asp
            660                 665                 670

Pro Ala Pro Thr Val Val Trp Gln Lys Thr Val Thr Gln Gly Lys Lys
            675                 680                 685

Ala Ser Ala Gly Pro His Pro Asp Ala Pro Glu Asp Ala Gly Ala Asp
            690                 695                 700

Glu Glu Trp Val Phe Asp Lys Lys Leu Leu Cys Glu Thr Glu Gly Arg
705                 710                 715                 720

Val Arg Val Glu Thr Thr Lys Asp Arg Ser Val Phe Thr Val Glu Gly
                725                 730                 735

Ala Glu Lys Glu Asp Glu Gly Val Tyr Thr Val Thr Val Lys Asn Pro
            740                 745                 750

Val Gly Glu Asp Gln Val Asn Leu Thr Val Lys Val Ile Asp Val Pro
            755                 760                 765

Asp Ala Pro Ala Ala Pro Lys Ile Ser Asn Val Gly Glu Asp Ser Cys
            770                 775                 780

Thr Val Gln Trp Glu Pro Pro Ala Tyr Asp Gly Gly Gln Pro Val Leu
785                 790                 795                 800

Gly Tyr Ile Leu Glu Arg Lys Lys Lys Ser Tyr Arg Trp Met Arg
                805                 810                 815

Leu Asn Phe Asp Leu Leu Arg Glu Leu Ser His Glu Ala Arg Arg Met
            820                 825                 830

Ile Glu Gly Val Ala Tyr Glu Met Arg Val Tyr Ala Val Asn Ala Val
            835                 840                 845

Gly Met Ser Arg Pro Ser Pro Ala Ser Gln Pro Phe Met Pro Ile Gly
            850                 855                 860

Pro Pro Gly Glu Pro Thr His Leu Ala Val Glu Asp Val Ser Asp Thr
865                 870                 875                 880

Thr Val Ser Leu Lys Trp Arg Pro Pro Glu Arg Val Gly Ala Gly Gly
                885                 890                 895

Leu Asp Gly Tyr Ser Val Glu Tyr Cys Gln Glu Gly Cys Ser Glu Trp
            900                 905                 910
```

Thr Pro Ala Leu Gln Gly Leu Thr Glu Arg Arg Ser Met Leu Val Lys
    915                 920                 925

Asp Leu Pro Thr Gly Ala Arg Leu Leu Phe Arg Val Arg Ala His Asn
930                 935                 940

Val Ala Gly Pro Gly Pro Ile Val Thr Lys Glu Pro Val Thr Val
945                 950                 955                 960

Gln Glu Ile Leu Gln Arg Pro Arg Leu Gln Leu Pro Arg His Leu Arg
                965                 970                 975

Gln Thr Ile Gln Lys Lys Val Gly Glu Pro Val Asn Leu Leu Ile Pro
            980                 985                 990

Phe Gln Gly Lys Pro Arg Pro Gln Val Thr Trp Thr Lys Glu Gly Gln
        995                 1000                1005

Pro Leu Ala Gly Glu Glu Val Ser Ile Arg Asn Ser Pro Thr Asp
    1010                1015                1020

Thr Ile Leu Phe Ile Arg Ala Arg Arg Thr His Ser Gly Thr
    1025                1030                1035

Tyr Gln Val Thr Val Arg Ile Glu Asn Met Glu Asp Lys Ala Thr
    1040                1045                1050

Leu Ile Leu Gln Ile Val Asp Lys Pro Ser Pro Pro Gln Asp Ile
    1055                1060                1065

Arg Ile Val Glu Thr Trp Gly Phe Asn Val Ala Leu Glu Trp Lys
    1070                1075                1080

Pro Pro Gln Asp Asp Gly Asn Thr Glu Ile Trp Gly Tyr Thr Val
    1085                1090                1095

Gln Lys Ala Asp Lys Lys Thr Met Glu Trp Phe Thr Val Leu Glu
    1100                1105                1110

His Tyr Arg Arg Thr His Cys Val Val Ser Glu Leu Ile Ile Gly
    1115                1120                1125

Asn Gly Tyr Tyr Phe Arg Val Phe Ser His Asn Met Val Gly Ser
    1130                1135                1140

Ser Asp Lys Ala Ala Ala Thr Lys Glu Pro Val Phe Ile Pro Arg
    1145                1150                1155

Pro Gly Ile Thr Tyr Glu Pro Pro Lys Tyr Lys Ala Leu Asp Phe
    1160                1165                1170

Ser Glu Ala Pro Ser Phe Thr Gln Pro Leu Ala Asn Arg Ser Ile
    1175                1180                1185

Ile Ala Gly Tyr Asn Ala Ile Leu Cys Cys Ala Val Arg Gly Ser
    1190                1195                1200

Pro Lys Pro Lys Ile Ser Trp Phe Lys Asn Gly Leu Asp Leu Gly
    1205                1210                1215

Glu Asp Ala Arg Phe Arg Met Phe Cys Lys Gln Gly Val Leu Thr
    1220                1225                1230

Leu Glu Ile Arg Lys Pro Cys Pro Tyr Asp Gly Gly Val Tyr Val
    1235                1240                1245

Cys Arg Ala Thr Asn Leu Gln Gly Glu Ala Gln Cys Glu Cys Arg
    1250                1255                1260

Leu Glu Val Arg Val Pro Gln
    1265                1270

<210> SEQ ID NO 11
<211> LENGTH: 2889
<212> TYPE: DNA
<213> ORGANISM: Mus musculus

<400> SEQUENCE: 11

```
atgccggagc cgggtaaaaa gccggttagc gcgttcaaca aaaaaccgcg tagcgcggaa      60
gtgaccgcgg gtagcgcggc ggtgtttgag gcggaaaccg agcgtagcgg cgttaaagtg     120
cgttggcaac gtgacggtag cgatattacc gcgaacgata atacggtct ggcggcggaa      180
ggcaagcgtc acaccctgac cgttcgtgat gcgagcccgg acgatcaggg tagctatgcg     240
gtgatcgcgg gcagcagcaa ggtgaaattt gacctgaaag ttaccgagcc ggctccgccg     300
gaaaaagcgg aaagcgaggt ggcgccgggt gcgccgaagg aagttccggc gccggcgacc     360
gagctggagg aaagcgtgag cagcccggaa ggcagcgtta gcgtgaccca ggatggtagc     420
gcggcggaac atcaaggtgc gccggatgat ccgatcggtc tgttcctgat gcgtccgcaa     480
gacggtgagg ttaccgtggg tggcagcatt gtgtttagcg cgcgtgttgc gggtgcgagc     540
ctgctgaaac cgccggtggt taagtggttc aagggcaaat gggtggatct gagcagcaaa     600
gttggtcagc acctgcaact gcacgacagc tacgatcgtg cgagcaaggt ttacctgttc     660
gaactgcaca ttaccgatgc gcagaccacc agcgcgggtg gctaccgttg cgaggttagc     720
accaaggaca aattcgatag ctgcaacttt aacctgaccg tgcacgaagc gatcggtagc     780
ggcgacctgg atctgcgtag cgcgtttcgt cgtaccagcc tggcgggtgc gggtcgtcgt     840
accagcgaca gccatgagga tgcgggcacc ctggatttca gcagcctgct gaagaaacgt     900
gatagctttc gtcgtgacag caaactggaa gcgccggcgg aggaagacgt ttgggagatc     960
ctgcgtcaag ctccgccgag cgaatacgag cgtattgcgt ccagcacgg tgtgaccgat    1020
ctgcgtggca tgctgaagcg tctgaagggt atgaagcagg acgaaaagaa agcaccgcg    1080
tttcagaaga aactggagcc ggcgtatcaa gtgaacaaag ccacaagat ccgtctgacc    1140
gtggaactgg cggaccccgga tgcggaagtg aaatggctga agaacggcca ggaaatccaa   1200
atgagcggta gcaaatacat tttcgagagc gttggtgcga agcgtaccct gaccattagc    1260
caatgcagcc tggcggacga tgcggcgtat cagtgcgtgg ttggtggcga aaatgcagc    1320
accgaactgt tcgtgaagga gccgccggtt ctgatcaccc gtagcctgga agatcagctg    1380
gttatggtgg tcaacgtgt ggaatttgag tgcgaagtta gcgaggaagg cgcgcaagtg    1440
aaatggctga aggacggtgt tgagctgacc cgtgaggaaa ccttcaaata ccgttttaag    1500
aaagatggtc gtaagcacca cctgatcatt aacgaagcga ccctggagga tgcgggtcac   1560
tatgcggttc gtaccagcgg tggccagagc ctggcggaac tgatcgtgca agaaaagaaa    1620
ctggaagtgt atcagagcat tgcggatctg gcggtgggtg cgaaagacca ggcggtgttc    1680
aagtgcgaag ttagcgatga gaacgttcgt ggtgtgtggc tgaaaaacgg caaggagctg    1740
gttccggaca accgtatcaa agtgagccac attggtcgtg ttcacaagct gaccatcgac    1800
gatgttaccc cggcggacga agcggattat agcttcgtgc cggagggctt tgcgtgcaac    1860
ctgagcgcga aactgcactt catgaagtg aagatcgact ttgttccgcg tcaggagccg    1920
ccgaaaattc atctggattg cccgggtagc accccgaca ccattgtggt tgtggcgggt    1980
aacaaactgc gtctggatgt gccgattagc ggcgacccgg cgccgaccgt tgtgtggcag    2040
aagaccgtga cccaaggtaa gaaagcgagc accggtccgc acccggatgc gccggaggat    2100
gcgggtgcgg acgaggaatg ggttttcgat aagaaactgc tgtgcgaaac cgaaggccgt    2160
gttcgtgtgg aaaccaccaa ggatcgtagc gttttaccg tggagggcgc ggagaaagaa    2220
gacgagggtg tttacaccgt taccgtgaag aacccggtgg gtgaagacca ggttaacctg    2280
accgttaaag ttattgatgt tccggatgcg ccggcggcgc cgaagattag caacgtgggt    2340
```

-continued

```
gaagatagct gcaccgttca atgggagccg ccggcgtatg atggtggcca gccggtgctg    2400
ggctatatcc tggagcgtaa gaaaaagaaa agctatcgtt ggatgcgtct gaacttcgac    2460
ctgctgcgtg aactgagcca cgaggcgcgt cgtatgattg aaggtgttgc gtacgagatg    2520
cgtgtttatg cggtgaacgc ggttggtatg agccgtccga gcccggcgag ccagccgttt    2580
atgccgattg gtccgccggg tgaaccgacc cacctggcgg tggaggacgt tagcgatacc    2640
accgtgagcc tgaaatggcg tccgccggaa cgtgttggtg cgggtggcct ggatggctac    2700
agcgtggaat attgccaaga gggctgcagc gaatggaccc cggcgctgca gggtctgacc    2760
gagcgtacca gcatgctggt taaagacctg ccgaccggtg cgcgtctgct gttccgtgtg    2820
cgtgcgcata acgttgcggg tccgggtggc ccgatcgtga ccaaggaacc ggttaccgtg    2880
caggagatt                                                          2889
```

<210> SEQ ID NO 12
<211> LENGTH: 963
<212> TYPE: PRT
<213> ORGANISM: Mus musculus

<400> SEQUENCE: 12

```
Met Pro Glu Pro Gly Lys Lys Pro Val Ser Ala Phe Asn Lys Lys Pro
1               5                   10                  15

Arg Ser Ala Glu Val Thr Ala Gly Ser Ala Ala Val Phe Glu Ala Glu
            20                  25                  30

Thr Glu Arg Ser Gly Val Lys Val Arg Trp Gln Arg Asp Gly Ser Asp
        35                  40                  45

Ile Thr Ala Asn Asp Lys Tyr Gly Leu Ala Ala Glu Gly Lys Arg His
    50                  55                  60

Thr Leu Thr Val Arg Asp Ala Ser Pro Asp Asp Gln Gly Ser Tyr Ala
65                  70                  75                  80

Val Ile Ala Gly Ser Ser Lys Val Lys Phe Asp Leu Lys Val Thr Glu
                85                  90                  95

Pro Ala Pro Pro Glu Lys Ala Glu Ser Glu Val Ala Pro Gly Ala Pro
            100                 105                 110

Lys Glu Val Pro Ala Pro Ala Thr Glu Leu Glu Glu Ser Val Ser Ser
        115                 120                 125

Pro Glu Gly Ser Val Ser Val Thr Gln Asp Gly Ser Ala Ala Glu His
    130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
            180                 185                 190

Lys Trp Val Asp Leu Ser Ser Lys Val Gly Gln His Leu Gln Leu His
        195                 200                 205

Asp Ser Tyr Asp Arg Ala Ser Lys Val Tyr Leu Phe Glu Leu His Ile
    210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Asn Phe Asn Leu Thr Val His Glu
                245                 250                 255

Ala Ile Gly Ser Gly Asp Leu Asp Leu Arg Ser Ala Phe Arg Arg Thr
            260                 265                 270
```

```
Ser Leu Ala Gly Ala Gly Arg Arg Thr Ser Asp Ser His Glu Asp Ala
    275                 280                 285

Gly Thr Leu Asp Phe Ser Ser Leu Leu Lys Lys Arg Asp Ser Phe Arg
    290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                    325                 330                 335

Gly Val Thr Asp Leu Arg Gly Met Leu Lys Arg Leu Lys Gly Met Lys
                340                 345                 350

Gln Asp Glu Lys Lys Ser Thr Ala Phe Gln Lys Lys Leu Glu Pro Ala
            355                 360                 365

Tyr Gln Val Asn Lys Gly His Lys Ile Arg Leu Thr Val Glu Leu Ala
        370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                    405                 410                 415

Leu Thr Ile Ser Gln Cys Ser Leu Ala Asp Asp Ala Ala Tyr Gln Cys
                420                 425                 430

Val Val Gly Gly Glu Lys Cys Ser Thr Glu Leu Phe Val Lys Glu Pro
            435                 440                 445

Pro Val Leu Ile Thr Arg Ser Leu Glu Asp Gln Leu Val Met Val Gly
        450                 455                 460

Gln Arg Val Glu Phe Glu Cys Glu Val Ser Glu Gly Ala Gln Val
465                 470                 475                 480

Lys Trp Leu Lys Asp Gly Val Glu Leu Thr Arg Glu Glu Thr Phe Lys
                    485                 490                 495

Tyr Arg Phe Lys Lys Asp Gly Arg Lys His His Leu Ile Ile Asn Glu
                500                 505                 510

Ala Thr Leu Glu Asp Ala Gly His Tyr Ala Val Arg Thr Ser Gly Gly
            515                 520                 525

Gln Ser Leu Ala Glu Leu Ile Val Gln Glu Lys Lys Leu Glu Val Tyr
        530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                    565                 570                 575

Gly Lys Glu Leu Val Pro Asp Asn Arg Ile Lys Val Ser His Ile Gly
                580                 585                 590

Arg Val His Lys Leu Thr Ile Asp Asp Val Thr Pro Ala Asp Glu Ala
            595                 600                 605

Asp Tyr Ser Phe Val Pro Glu Gly Phe Ala Cys Asn Leu Ser Ala Lys
        610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
                    645                 650                 655

Val Val Ala Gly Asn Lys Leu Arg Leu Asp Val Pro Ile Ser Gly Asp
                660                 665                 670

Pro Ala Pro Thr Val Val Trp Gln Lys Thr Val Thr Gln Gly Lys Lys
            675                 680                 685
```

-continued

```
Ala Ser Thr Gly Pro His Pro Asp Ala Pro Glu Asp Ala Gly Ala Asp
    690                 695                 700

Glu Glu Trp Val Phe Asp Lys Lys Leu Leu Cys Glu Thr Glu Gly Arg
705                 710                 715                 720

Val Arg Val Glu Thr Thr Lys Asp Arg Ser Val Phe Thr Val Glu Gly
            725                 730                 735

Ala Glu Lys Glu Asp Glu Gly Val Tyr Thr Val Thr Val Lys Asn Pro
        740                 745                 750

Val Gly Glu Asp Gln Val Asn Leu Thr Val Lys Val Ile Asp Val Pro
    755                 760                 765

Asp Ala Pro Ala Ala Pro Lys Ile Ser Asn Val Gly Glu Asp Ser Cys
770                 775                 780

Thr Val Gln Trp Glu Pro Pro Ala Tyr Asp Gly Gly Gln Pro Val Leu
785                 790                 795                 800

Gly Tyr Ile Leu Glu Arg Lys Lys Lys Ser Tyr Arg Trp Met Arg
            805                 810                 815

Leu Asn Phe Asp Leu Leu Arg Glu Leu Ser His Glu Ala Arg Arg Met
        820                 825                 830

Ile Glu Gly Val Ala Tyr Glu Met Arg Val Tyr Ala Val Asn Ala Val
    835                 840                 845

Gly Met Ser Arg Pro Ser Pro Ala Ser Gln Pro Phe Met Pro Ile Gly
850                 855                 860

Pro Pro Gly Glu Pro Thr His Leu Ala Val Glu Asp Val Ser Asp Thr
865                 870                 875                 880

Thr Val Ser Leu Lys Trp Arg Pro Pro Glu Arg Val Gly Ala Gly Gly
            885                 890                 895

Leu Asp Gly Tyr Ser Val Glu Tyr Cys Gln Glu Gly Cys Ser Glu Trp
        900                 905                 910

Thr Pro Ala Leu Gln Gly Leu Thr Glu Arg Thr Ser Met Leu Val Lys
    915                 920                 925

Asp Leu Pro Thr Gly Ala Arg Leu Leu Phe Arg Val Arg Ala His Asn
930                 935                 940

Val Ala Gly Pro Gly Gly Pro Ile Val Thr Lys Glu Pro Val Thr Val
945                 950                 955                 960

Gln Glu Ile
```

<210> SEQ ID NO 13
<211> LENGTH: 1374
<212> TYPE: PRT
<213> ORGANISM: Artificial Sequence
<220> FEATURE:
<223> OTHER INFORMATION: cMyBP-c with SpyCatcher and SpyTag inserted in
      between domains C7 and C8 of cMyBP-c
<220> FEATURE:
<221> NAME/KEY: MISC_FEATURE
<222> LOCATION: (964)..(1053)
<223> OTHER INFORMATION: SpyCatcher sequence
<220> FEATURE:
<221> NAME/KEY: MISC_FEATURE
<222> LOCATION: (1055)..(1067)
<223> OTHER INFORMATION: SpyTag sequence

<400> SEQUENCE: 13

```
Met Pro Glu Pro Gly Lys Lys Pro Val Ser Ala Phe Asn Lys Lys Pro
1               5                   10                  15

Arg Ser Ala Glu Val Thr Ala Gly Ser Ala Ala Val Phe Glu Ala Glu
            20                  25                  30

Thr Glu Arg Ser Gly Val Lys Val Arg Trp Gln Arg Asp Gly Ser Asp
```

```
                35                  40                  45
Ile Thr Ala Asn Asp Lys Tyr Gly Leu Ala Ala Glu Gly Lys Arg His
 50                  55                  60

Thr Leu Thr Val Arg Asp Ala Ser Pro Asp Gln Gly Ser Tyr Ala
 65                  70                  75                  80

Val Ile Ala Gly Ser Lys Val Lys Phe Asp Leu Lys Val Thr Glu
                 85                  90                  95

Pro Ala Pro Glu Lys Ala Glu Ser Glu Val Ala Pro Gly Ala Pro
                100                 105                 110

Lys Glu Val Pro Ala Pro Thr Glu Leu Glu Ser Val Ser Ser
                115                 120                 125

Pro Glu Gly Ser Val Ser Val Thr Gln Asp Gly Ser Ala Ala Glu His
                130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
                180                 185                 190

Lys Trp Val Asp Leu Ser Ser Lys Val Gly Gln His Leu Gln Leu His
                195                 200                 205

Asp Ser Tyr Asp Arg Ala Ser Lys Val Tyr Leu Phe Glu Leu His Ile
210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Asn Phe Asn Leu Thr Val His Glu
                245                 250                 255

Ala Ile Gly Ser Gly Asp Leu Asp Leu Arg Ser Ala Phe Arg Arg Thr
                260                 265                 270

Ser Leu Ala Gly Ala Gly Arg Arg Thr Ser Asp Ser His Glu Asp Ala
                275                 280                 285

Gly Thr Leu Asp Phe Ser Ser Leu Leu Lys Lys Arg Asp Ser Phe Arg
                290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                325                 330                 335

Gly Val Thr Asp Leu Arg Gly Met Leu Lys Arg Leu Lys Gly Met Lys
                340                 345                 350

Gln Asp Glu Lys Lys Ser Thr Ala Phe Gln Lys Lys Leu Glu Pro Ala
                355                 360                 365

Tyr Gln Val Asn Lys Gly His Lys Ile Arg Leu Thr Val Glu Leu Ala
                370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Asp Ala Ala Tyr Gln Cys
                420                 425                 430

Val Val Gly Gly Glu Lys Cys Ser Thr Glu Leu Phe Val Lys Glu Pro
                435                 440                 445

Pro Val Leu Ile Thr Arg Ser Leu Glu Asp Gln Leu Val Met Val Gly
                450                 455                 460
```

-continued

```
Gln Arg Val Glu Phe Glu Cys Glu Val Ser Glu Gly Ala Gln Val
465                 470                 475                 480

Lys Trp Leu Lys Asp Gly Val Glu Leu Thr Arg Glu Thr Phe Lys
            485                 490                 495

Tyr Arg Phe Lys Lys Asp Gly Arg Lys His His Leu Ile Ile Asn Glu
            500                 505                 510

Ala Thr Leu Glu Asp Ala Gly His Tyr Ala Val Arg Thr Ser Gly Gly
            515                 520                 525

Gln Ser Leu Ala Glu Leu Ile Val Gln Glu Lys Lys Leu Glu Val Tyr
            530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                565                 570                 575

Gly Lys Glu Leu Val Pro Asp Asn Arg Ile Lys Val Ser His Ile Gly
            580                 585                 590

Arg Val His Lys Leu Thr Ile Asp Asp Val Thr Pro Ala Asp Glu Ala
            595                 600                 605

Asp Tyr Ser Phe Val Pro Glu Gly Phe Ala Cys Asn Leu Ser Ala Lys
610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
            645                 650                 655

Val Val Ala Gly Asn Lys Leu Arg Leu Asp Val Pro Ile Ser Gly Asp
            660                 665                 670

Pro Ala Pro Thr Val Val Trp Gln Lys Thr Val Thr Gln Gly Lys Lys
            675                 680                 685

Ala Ser Thr Gly Pro His Pro Asp Ala Pro Glu Asp Ala Gly Ala Asp
            690                 695                 700

Glu Glu Trp Val Phe Asp Lys Lys Leu Leu Cys Glu Thr Glu Gly Arg
705                 710                 715                 720

Val Arg Val Glu Thr Thr Lys Asp Arg Ser Val Phe Thr Val Glu Gly
                725                 730                 735

Ala Glu Lys Glu Asp Glu Gly Val Tyr Thr Val Thr Val Lys Asn Pro
            740                 745                 750

Val Gly Glu Asp Gln Val Asn Leu Thr Val Lys Val Ile Asp Val Pro
            755                 760                 765

Asp Ala Pro Ala Ala Pro Lys Ile Ser Asn Val Gly Glu Asp Ser Cys
770                 775                 780

Thr Val Gln Trp Glu Pro Pro Ala Tyr Asp Gly Gly Gln Pro Val Leu
785                 790                 795                 800

Gly Tyr Ile Leu Glu Arg Lys Lys Lys Ser Tyr Arg Trp Met Arg
            805                 810                 815

Leu Asn Phe Asp Leu Leu Arg Glu Leu Ser His Glu Ala Arg Arg Met
            820                 825                 830

Ile Glu Gly Val Ala Tyr Glu Met Arg Val Tyr Ala Val Asn Ala Val
            835                 840                 845

Gly Met Ser Arg Pro Ser Pro Ala Ser Gln Pro Phe Met Pro Ile Gly
            850                 855                 860

Pro Pro Gly Glu Pro Thr His Leu Ala Val Glu Asp Val Ser Asp Thr
865                 870                 875                 880
```

```
Thr Val Ser Leu Lys Trp Arg Pro Glu Arg Val Gly Ala Gly Gly
                885                 890                 895

Leu Asp Gly Tyr Ser Val Glu Tyr Cys Gln Glu Gly Cys Ser Glu Trp
                900                 905                 910

Thr Pro Ala Leu Gln Gly Leu Thr Glu Arg Thr Ser Met Leu Val Lys
                915                 920                 925

Asp Leu Pro Thr Gly Ala Arg Leu Leu Phe Arg Val Arg Ala His Asn
            930                 935                 940

Val Ala Gly Pro Gly Pro Ile Val Thr Lys Glu Pro Val Thr Val
945                 950                 955                 960

Gln Glu Ile Ser Gly Asp Ser Ala Thr His Ile Lys Phe Ser Lys Arg
                965                 970                 975

Asp Glu Asp Gly Lys Glu Leu Ala Gly Ala Thr Met Glu Leu Arg Asp
                980                 985                 990

Ser Ser Gly Lys Thr Ile Ser Thr Trp Ile Ser Asp Gly Gln Val Lys
                995                 1000                1005

Asp Phe Tyr Leu Tyr Pro Gly Lys Tyr Thr Phe Val Glu Thr Ala
        1010                1015                1020

Ala Pro Asp Gly Tyr Glu Val Ala Thr Ala Ile Thr Phe Thr Val
        1025                1030                1035

Asn Glu Gln Gly Gln Val Thr Val Asn Gly Lys Ala Thr Lys Gly
        1040                1045                1050

Gly Ala His Ile Val Met Val Asp Ala Tyr Lys Pro Thr Lys Leu
        1055                1060                1065

Gln Arg Pro Arg Leu Gln Leu Pro Arg His Leu Arg Gln Thr Ile
        1070                1075                1080

Gln Lys Lys Val Gly Glu Pro Val Asn Leu Leu Ile Pro Phe Gln
        1085                1090                1095

Gly Lys Pro Arg Pro Gln Val Thr Trp Thr Lys Glu Gly Gln Pro
        1100                1105                1110

Leu Ala Gly Glu Glu Val Ser Ile Arg Asn Ser Pro Thr Asp Thr
        1115                1120                1125

Ile Leu Phe Ile Arg Ala Ala Arg Arg Thr His Ser Gly Thr Tyr
        1130                1135                1140

Gln Val Thr Val Arg Ile Glu Asn Met Glu Asp Lys Ala Thr Leu
        1145                1150                1155

Ile Leu Gln Ile Val Asp Lys Pro Ser Pro Pro Gln Asp Ile Arg
        1160                1165                1170

Ile Val Glu Thr Trp Gly Phe Asn Val Ala Leu Glu Trp Lys Pro
        1175                1180                1185

Pro Gln Asp Asp Gly Asn Thr Glu Ile Trp Gly Tyr Thr Val Gln
        1190                1195                1200

Lys Ala Asp Lys Lys Thr Met Glu Trp Phe Thr Val Leu Glu His
        1205                1210                1215

Tyr Arg Arg Thr His Cys Val Val Ser Glu Leu Ile Ile Gly Asn
        1220                1225                1230

Gly Tyr Tyr Phe Arg Val Phe Ser His Asn Met Val Gly Ser Ser
        1235                1240                1245

Asp Lys Ala Ala Ala Thr Lys Glu Pro Val Phe Ile Pro Arg Pro
        1250                1255                1260

Gly Ile Thr Tyr Glu Pro Pro Lys Tyr Lys Ala Leu Asp Phe Ser
        1265                1270                1275

Glu Ala Pro Ser Phe Thr Gln Pro Leu Ala Asn Arg Ser Ile Ile
```

```
                1280                1285                1290
Ala Gly Tyr Asn Ala Ile Leu Cys Cys Ala Val Arg Gly Ser Pro
        1295                1300            1305

Lys Pro Lys Ile Ser Trp Phe Lys Asn Gly Leu Asp Leu Gly Glu
    1310                1315            1320

Asp Ala Arg Phe Arg Met Phe Cys Lys Gln Gly Val Leu Thr Leu
    1325                1330            1335

Glu Ile Arg Lys Pro Cys Pro Tyr Asp Gly Gly Val Tyr Val Cys
    1340                1345            1350

Arg Ala Thr Asn Leu Gln Gly Glu Ala Gln Cys Glu Cys Arg Leu
    1355                1360            1365

Glu Val Arg Val Pro Gln
    1370

<210> SEQ ID NO 14
<211> LENGTH: 7
<212> TYPE: PRT
<213> ORGANISM: Mus musculus

<400> SEQUENCE: 14

Val Gln Glu Ile Leu Gln Arg
1               5

<210> SEQ ID NO 15
<211> LENGTH: 8
<212> TYPE: PRT
<213> ORGANISM: Mus musculus

<400> SEQUENCE: 15

Pro Arg Leu Gln Leu Pro Arg His
1               5
```